(12) United States Patent
Liu et al.

(10) Patent No.: US 8,759,028 B2
(45) Date of Patent: Jun. 24, 2014

(54) EXPRESSION CASSETTE, RECOMBINANT HOST CELL AND PROCESS FOR PRODUCING A TARGET PROTEIN

(75) Inventors: Yung-Chuan Liu, Taichung (TW); Jiun-Yan Wu, Taichung (TW); Chia-Chi Lin, Hsinchu (TW)

(73) Assignee: National Chung-Hsing University, Taichung (TW)

( * ) Notice: Subject to any disclaimer, the term of this patent is extended or adjusted under 35 U.S.C. 154(b) by 78 days.

(21) Appl. No.: 13/284,800

(22) Filed: Oct. 28, 2011

(65) Prior Publication Data
US 2012/0107875 A1 May 3, 2012

(30) Foreign Application Priority Data

Oct. 29, 2010 (TW) ................................ 99137264 A

(51) Int. Cl.
*C12N 9/86* (2006.01)
*C12N 15/62* (2006.01)
*C12P 21/00* (2006.01)

(52) U.S. Cl.
USPC .................... 435/69.7; 435/252.33; 435/320.1

(58) Field of Classification Search
None
See application file for complete search history.

(56) References Cited

PUBLICATIONS

Esipov et al. Production of recombinant human epidermal growth factor using Ssp dnaB mini-intein system. Protein Expression and Purification, vol. 61, issue 1, Sep. 2008, pp. 1-6 see attached.*

Jung et al (Surface display of Zymomonas mobilis levansucrase by using the ice-nucleation protein of Pseudomonas syringae. Nat. Biotechnology Jun. 1998:16 (6):576-80).*

Myscofski et al (Cleavage and Purification of intein proteins using the *Streptococcus gordonii* SPEX system. Preparative Biochemistry and Biotechnology Received: Jan. 24, 2001, Accepted: Feb. 22, 2001, Published online: Aug. 18, 2006.*

"Functional Display of Foreign Protein on Surface of *Escherichia coli* Using N-Terminal Domain of Ice Nucleation Protein", Wiley InterScience, Dec. 10, 2003, 8 pages.

"Autolysin of *Bacillus thuringiensis* for the Development of a Cell Surface Display System", Huazhong Agricultural University Master's Thesis, Jun. 1, 2009 and an English abstract on p. 3 and 4 of the thesis, 93 pages.

"Purification of green fluorescent protein using a two-intein system", Appl Microbial Biotechnol (2008), 77:1175-1180, 6 pages.

* cited by examiner

*Primary Examiner* — Kagnew H Gebreyesus
(74) *Attorney, Agent, or Firm* — Kilpatrick Townsend & Stockton LLP

(57) ABSTRACT

Disclosed herein is a process for producing a target protein, in which a recombinant polynucleotide is constructed to encode a fusion protein including: (i) an anchoring protein that includes a N-terminal amino acid sequence of an ice nucleation protein, so that the fusion protein, once expressed in the host cell, is directed by the anchoring protein to be anchored and exposed on the outer membrane of the host cell; (ii) the target protein; and (iii) a self-splicing protein that includes a first end fused with the anchoring protein and a second end fused with the target protein, wherein the self-splicing protein includes a N-terminal or C-terminal amino acid sequence of an intein protein at the second end thereof, such that upon an environmental stimulus, the self-splicing protein exerts a self-cleavage at the second end thereof to release the target protein from the fusion protein.

22 Claims, 10 Drawing Sheets

SEQUENCE LISTING

<160> NUMBER OF SEQ ID NOS: 11

<210> SEQ ID NO 1
<211> LENGTH: 5297
<212> TYPE: DNA
<213> ORGANISM: artificial sequence
<220> FEATURE:
<223> OTHER INFORMATION: plasmid pJO1-OSP1
<220> FEATURE:
<221> NAME/KEY: Ssp dnaB gene
<222> LOCATION: (4578)..(5057)

<400> SEQUENCE: 1

| | | | | | |
|---|---|---|---|---|---|
| tcgcgagctt | ggcactggcc | gtcgttttac | aacgtcgtga | ctgggaaaac | cctggcgtta | 60 |
| cccaacttaa | tcgccttgca | gcacatcccc | ctttcgccag | ctggcgtaat | agcgaagagg | 120 |
| cccgcaccga | tcgcccttcc | caacagttgc | gcagcctgaa | tggcgaatgg | cgctagcagc | 180 |
| acgccatagt | gactggcgat | gctgtcggaa | tggacgataa | ttcgacagta | agacgggtaa | 240 |
| gcctgttgat | gataccgctg | ccttactggg | tgcattagcc | agtctgaatg | acctgtcacg | 300 |
| ggataatccg | aagtggtcag | actggaaaat | cagagggcag | gaactgcgaa | cagcaaaaag | 360 |
| tcagatagca | ccacatagca | gacccgccat | aaaacgccct | gagagcccgt | gacgggcttt | 420 |
| tcttgtatta | tgggtagttt | ccttgcatga | atccataaaa | ggcgcctgta | gtgccattta | 480 |
| cccccattca | ctgccagagc | cgtgagcgca | gcgaactgaa | tgtcacgaaa | aagacagcga | 540 |
| ctcaggtgcc | tgatggtcgg | agacaaaagg | aatattcagc | gatttgcccg | agaattatcc | 600 |
| cgcaagaggc | ccggcagtca | ggtggcactt | tcggggaaa | tgtgcgcgga | accctatt | 660 |
| gtttattttt | ctaaatacat | tcaaatatgt | atccgctcat | gagacaataa | ccctgataaa | 720 |
| tgcttcaata | atattgaaaa | aggaagagta | tgagtattca | acatttccgt | gtcgccctta | 780 |
| ttccctttt | tgcggcattt | tgccttcctg | ttttgctca | cccagaaacg | ctggtgaaag | 840 |
| taaaagatgc | tgaagatcag | ttgggtgcac | gagtgggtta | catcgaactg | gatctcaaca | 900 |
| gcggtaagat | ccttgagagt | tttcgccccg | aagaacgttt | tccaatgatg | agcacttta | 960 |
| aagttctgct | atgtggcgcg | gtattatccc | gtattgacgc | cgggcaagag | caactcggtc | 1020 |
| gccgcataca | ctattctcag | aatgacttgg | ttgagtactc | accagtcaca | gaaaagcatc | 1080 |
| ttacggatgg | catgacagta | agagaattat | gcagtgctgc | cataaccatg | agtgataaca | 1140 |
| ctgcggccaa | cttacttctg | acaacgatcg | gaggaccgaa | ggagctaacc | gctttttgc | 1200 |
| acaacatggg | ggatcatgta | actcgccttg | atcgttggga | accggagctg | aatgaagcca | 1260 |
| taccaaacga | cgagcgtgac | accacgatgc | ctgtagcaat | ggcaacaacg | ttgcgcaaac | 1320 |
| tattaactgg | cgaactactt | actctagctt | cccggcaaca | attaatagac | tggatggagg | 1380 |
| cggataaagt | tgcaggacca | cttctgcgct | cggcccttcc | ggctggctgg | tttattgctg | 1440 |
| ataaatctgg | agccggtgag | cgtgggtctc | gcggtatcat | tgcagcactg | gggccagatg | 1500 |

```
gtaagccctc ccgtatcgta gttatctaca cgacggggag tcaggcaact atggatgaac    1560
gaaatagaca gatcgctgag ataggtgcct cactgattaa gcattggtaa ctgtcagacc    1620
aagtttactc atatatactt tagattgatt taaaacttca ttttttaattt aaaaggatct   1680 aggtgaagat ccttttttgat aatctcatga ccaaaatccc ttaacgtgag ttttcgttcc   1740
actgagcgtc agaccccgta gaaaagatca aaggatcttc ttgagatcct ttttttctgc    1800
gcgtaatctg ctgcttgcaa acaaaaaaac caccgctacc agcggtggtt tgtttgccgg    1860
atcaagagct accaactctt tttccgaagg taactggctt cagcagagcg cagataccaa    1920
atactgttct tctagtgtag ccgtagttag gccaccactt caagaactct gtagcaccgc    1980
ctacatacct cgctctgcta atcctgttac cagtggctgc tgccagtggc gataagtcgt    2040
gtcttaccgg gttggactca agacgatagt taccggataa ggcgcagcgg tcgggctgaa   2100
cggggggttc gtgcacacag cccagcttgg agcgaacgac ctacaccgaa ctgagatacc    2160
tacagcgtga gcattgagaa agcgccacgc ttcccgaagg gagaaaggcg gacaggtatc    2220
cggtaagcgg cagggtcgga acaggagagc gcacgaggga gcttccaggg ggaaacgcct    2280
ggtatcttta tagtcctgtc gggtttcgcc acctctgact tgagcgtcga ttttgtgat    2340 gctcgtcagg gggcggagc ctatggaaaa acgccagcaa cgcggccttt ttacggttcc     2400
tggccttttg ctggccttttt gctcacatgt tctttcctgc gttatcccct gattctgtgg   2460
ataaccgtat taccgccttt gagtgagctg ataccgctcg ccgcagccga acgaccgagc    2520
gcagcgagtc agtgagcgag gaagctgcag cctaatgagt gagctaactt acattaattg    2580
cgttgcgctc actgcccgct ttccagtcgg gaaacctgtc gtgccagctg cattaatgaa    2640
tcggccaacg cgcggggaga ggcggtttgc gtattgggcg ccagggtggt ttttcttttc    2700
accagtgaga cgggcaacag ctgattgccc ttcaccgcct ggccctgaga gagttgcagc    2760
aagcggtcca cgctggtttg ccccagcagg cgaaaatcct gtttgatggt ggttaacggc    2820
gggatataac atgagctgtc ttcggtatcg tcgtatccca ctaccgagat atccgcacca    2880
acgcgcagcc cggactcggt aatggcgcgc attgcgccca gcgccatctg atcgttggca    2940
accagcatcg cagtgggaac gatgccctca ttcagcattt gcatggtttg ttgaaaaccg    3000
gacatggcac tccagtcgcc ttcccgttcc gctatcggct gaatttgatt gcgagtgaga    3060
tatttatgcc agccaccag acgcagacgc gccgagacag aacttaatgg gcccgctaac     3120
agcgcgattt gctggtgacc caatgcgacc agatgctcca cgcccagtcg cgtaccgtct    3180
tcatgggaga aaataatact gttgatgggt gtctggtcag agacatcaag aaataacgcc    3240
ggaacattag tgcaggcagc ttccacagca atggcatcct ggtcatccag cggatagtta    3300
atgatcagcc cactgacgcg ttgcgcgaga agattgtgca ccgccgcttt acaggcttcg    3360
acgccgcttc gttctaccat cgacaccacc acgctggcac ccagttgatc ggcgcgagat    3420
ttaatcgccg cgacaatttg cgacggcgcg tgcagggcca gactggaggt ggcaacgcca    3480
atcagcaacg actgtttgcc cgccagttgt tgtgccacgc ggttgggaat gtaattcagc    3540
tccgccatcg ccgcttccac ttttcccgc gttttcgcag aaacgtggct ggcctggttc     3600
accacgcggg aaacggtctg ataagagaca ccggcatact ctgcgacatc gtataacgtt    3660
actggtttca cattcaccac cctgaattga ctctcttccg ggcgctatca tgccataccg    3720
cgaaaggttt tgcgccattc gatggtgtcc gggatctcga cgctctccct tatgcgactc    3780
ctgcattagg aagcagccca gtagtaggtt gaggccgttg agcaccgccg ccgcaaggaa    3840
tggtgcatgc aaggagatgg cgcccaacag tcccccggcc acggggcctg ccaccatacc    3900
```

```
cacgccgaaa caagcgctca tgagcccgaa gtggcgagcc cgatcttccc catcggtgat    3960
gtcggcgata taggcgccag caaccgcacc tgtggcgccg gtgatgccgg ccacgatgcg    4020
tccggcgtag aggatcgaga tcgatctcga tcccgcgaaa ttaatacgac tcactatagg    4080
ggaattgtga gcggataaca attcccctct agaaataatt tgtttaact ttaagaagga    4140 gatatacata tggctgagca ttatggtcaa caacagcaga ccagggcgcc tcacctgcag    4200
ctgcagccgc gcgcccagcg ggtagtgaag gcggccaccg ccgtgacagc cggcggctcg    4260
cttctcgtcc tctctggcct cactttagcc ggaactgtta ttgcgctcac catcgccact    4320
ccgctgcttg tgatctttag ccccgttctg gtgccggcgg tcataaccat tttcttgctg    4380
ggtgcgggtt ttctggcatc cggaggcttc ggcgtggcgg cgctgagtgt gctgtcgtgg    4440
atttacagat atctgacagg gaaacacccg ccggggcgg atcagctgga atcggcaaag    4500
acgaagctgg cgagcaaggc gcgagagatg aaggataggg cagagcagtt ctcgcagcag    4560
cctgttgcgg ggtctccatg gtgcgcgagt ccggagctat tctggcgat agtctgatca    4620 gcctggctag cacaggaaaa agagtttcta ttaaagattt gttagatgaa aaagattttg    4680
aaatatgggc aattaatgaa cagacgatga agctagaatc agctaaagtt agtcgtgtat    4740
tttgtactgg caaaaagcta gtttatattc taaaaactcg actaggtaga actatcaagg    4800
caacagcaaa tcatagattt ttaactattg atggttggaa aagattagat gagctatctt    4860
taaaagagca tattgctcta ccccgtaaac tagaaagctc ctctttacaa ttgtcaccag    4920
aaatagaaaa gttgtctcag agtgatattt actgggactc catcgtttct attacgaga    4980 ctggagtcga agaggttttt gatttgactg tgccaggacc acataacttt gtcgcgaatg    5040
acatcattgt acacaacgga agagccggat ccgaattcga gctccgtcga caagcttgcg    5100
gccgcactcg agcaccacca ccaccaccac tgagatccgg ctgctaacaa agcccgaaag    5160
gaagctgagt tggctgctgc caccgctgag caataactag cataaccct tggggcctct    5220 aaacgggtct tgaggggttt tttgctgaaa ggaggaacta tatccggatt ggcgaatggg    5280
acgcgccctg taggcct                                                  5297
```

<210> SEQ ID NO 2
<211> LENGTH: 8132
<212> TYPE: DNA
<213> ORGANISM: artificial sequence
<220> FEATURE:
<223> OTHER INFORMATION: plasmid pInaXNC1-aglA2
<220> FEATURE:
<221> NAME/KEY: inaNC gene
<222> LOCATION: (5131)..(5871)
<220> FEATURE:
<221> NAME/KEY: restriction_site
<222> LOCATION: (5872)..(5877)
<223> OTHER INFORMATION: recognized by EcoRI
<220> FEATURE:
<221> NAME/KEY: restriction_site
<222> LOCATION: (7971)..(7976)
<223> OTHER INFORMATION: recognized by XhoI
<300> PUBLICATION INFORMATION:
<301> AUTHORS: Po-Hung Wu et al.
<303> JOURNAL: Biotechnology and Bioengineering
<304> VOLUME: 95
<306> PAGES: 1138-1149
<307> DATE: 2006-07-01

<400> SEQUENCE: 2

```
tggcgaatgg gacgcgccct gtagcggcgc attaagcgcg gcgggtgtgg tggttacgcg    60
cagcgtgacc gctacacttg ccagcgccct agcgcccgct cctttcgctt tcttcccttc   120
```

```
ctttctcgcc acgttcgccg gctttccccg tcaagctcta aatcgggggc tccctttagg      180
gttccgattt agtgctttac ggcacctcga ccccaaaaaa cttgattagg gtgatggttc      240
acgtagtggg ccatcgccct gatagacggt ttttcgccct ttgacgttgg agtccacgtt      300
ctttaatagt ggactcttgt tccaaactgg aacaacactc aaccctatct cggtctattc      360
ttttgattta aagggatttt tgccgatttc ggcctattgg ttaaaaaatg agctgattta      420
acaaaatttt aacgcgaatt ttaacaaaat attaacgttt acaatttcag gtggcacttt      480
tcggggaaat gtgcgcggaa cccctatttg tttattttc taaatacatt caaatatgta      540
tccgctcatg aattaattct tagaaaaact catcgagcat caaatgaaac tgcaatttat      600
tcatatcagg attatcaata ccatattttt gaaaaagccg tttctgtaat gaaggagaaa      660
actcaccgag gcagttccat aggatggcaa gatcctggta tcggtctgcg attccgactc      720
gtccaacatc aatacaacct attaatttcc cctcgtcaaa aataaggtta tcaagtgaga      780
aatcaccatg agtgacgact gaatccggtg agaatggcaa aagtttatgc atttcttcc      840
agacttgttc aacaggccag ccattacgct cgtcatcaaa atcactcgca tcaaccaaac      900
cgttattcat tcgtgattgc gcctgagcga cgaaatac gcgatcgctg ttaaaaggac       960
aattacaaac aggaatcgaa tgcaaccggc gcaggaacac tgccagcgca tcaacaatat     1020
tttcacctga atcaggatat tcttctaata cctggaatgc tgtttcccg gggatcgcag     1080
tggtgagtaa ccatgcatca tcaggagtac ggataaaatg cttgatggtc ggaagaggca     1140
taaattccgt cagccagttt agtctgacca tctcatctgt aacatcattg gcaacgctac     1200
ctttgccatg tttcagaaac aactctggcg catcgggctt cccatacaat cgatagattg     1260
tcgcacctga ttgcccgaca ttatcgcgag cccatttata cccatataaa tcagcatcca     1320
tgttggaatt taatcgcggc ctagagcaag acgtttcccg ttgaatatgg ctcataacac     1380
cccttgtatt actgtttatg taagcagaca gttttattgt tcatgaccaa atcccttaa     1440
cgtgagtttt cgttccactg agcgtcagac cccgtagaaa agatcaaagg atcttcttga     1500
gatccttttt ttctgcgcgt aatctgctgc ttgcaaacaa aaaaaccacc gctaccagcg     1560
gtggtttgtt tgccggatca agagctacca actctttttc cgaaggtaac tggcttcagc     1620
agagcgcaga taccaaatac tgtccttcta gtgtagccgt agttaggcca ccacttcaag     1680
aactctgtag caccgcctac atacctcgct ctgctaatcc tgttaccagt ggctgctgcc     1740
agtggcgata agtcgtgtct taccgggttg gactcaagac gatagttacc ggataaggcg     1800
cagcggtcgg gctgaacggg gggttcgtgc acacagccca gcttggagcg aacgacctac     1860
accgaactga gatacctaca gcgtgagcta tgagaaagcg ccacgcttcc gaagggaga     1920
aaggcggaca ggtatccggt aagcggcagg gtcggaacag gagagcgcac gagggagctt     1980
ccagggggaa acgcctggta tctttatagt cctgtcgggt ttcgccacct ctgacttgag     2040
cgtcgatttt tgtgatgctc gtcagggggg cggagcctat ggaaaaacgc cagcaacgcg     2100
gcctttttac ggttcctggc cttttgctgg ccttttgctc acatgttctt tcctgcgtta     2160
tcccctgatt ctgtggataa ccgtattacc gcctttgagt gagctgatac cgctcgccgc     2220
agccgaacga ccgagcgcag cgagtcagtg agcgaggaag cggaagagcg cctgatgcgg     2280
tattttctcc ttacgcatct gtgcggtatt tcacaccgca tatatggtgc actctcagta     2340
caatctgctc tgatgccgca tagttaagcc agtatacact ccgctatcgc tacgtgactg     2400
ggtcatggct gcgccccgac acccgccaac acccgctgac gcgccctgac gggcttgtct     2460
```

```
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aaggggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380 gggcagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
```

```
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa cttaagaag gagatatacc atgggcagca gccatcatca tcatcatcac    5100
agcagcggcc tggtgccgcg cggcagccat atgaatcgcg aaaaagtctt ggcattacgc    5160
acttgcacga caacatgtc cgatcattgc gggctgatct ggccactgtc cggcatcgtc    5220
gaatgtcggc attggcaacc cagcatcaaa caggaaaacg gcttgaccgg cttgttgtgg    5280
ggacagggca ccaatgcgca tctgaacatg catgccgacg cgcattgggt cgtctgcatg    5340
gtggacaccg ccgacatcat ctggctgggc gaagagggaa tgatcaagtt ccccagggcg    5400
gaggtggtct acgccggcaa ccgtgcaggc gcgatgagct gcatcgccgc cggcatcgag    5460
caacattcgc cacccaagcc cgagccgcct gcagacagtg tgattgctgc ggagttcact    5520
cccaaggcgg cgcatgcgca attcacggcg cccatcgttg aaagcggtgc gcattccacc    5580
gcgccactgc catcgccgcc taatggcatc ggcccacaag ccgcgcagcc gtcaaatgcg    5640
atcctgcgta cccgcgaaat cagatccttc cgatgctggg acggcaagcg ctacaccaac    5700
atcattgcca agaccggaga ggagggcgtg gaggccgaca tcgcctatca ggtcgacgac    5760
gacaagaacg tggtcgaaaa attcgacgat ccgttcgaca ccatcgtgct tcggcatgat    5820
ggcgggcccg cttctgcggc cgatcacgcg ctggtggagc aggcgcccaa tgaattcatg    5880
ccgctgtctt cgcgtcgagt acgctcgaca ttgggtgccg cgtggatcgc gcgcctgctg    5940
gtgatcgcca cactgggcgg cgccgctgcc actgcccagg ccgaggatgc gatcgacgtt    6000
gcctcgcccg gcaagatttt gcaggtgacc gtggaagtgg atggcggcac gccgtactac    6060
cgtgtgcagc ggctgggtga ccggtggtg gagcgctcgc ggcttggatt tcagctgcgc    6120
gatgggcgcc tggatcgcgg cctgcaggtg ctgtcgcagg cgcgcagcag ccacgatgac    6180
acctgggaac aaccctgggg cgaaacccgg ctggtgcgca accactacaa cgaattgcgc    6240
gtgagccttg gcgagcgcga gggcgcgcaa cggcgcttcg atgtgatcgt gcgtgtgtac    6300
gacgacgggc tcggcctgcg ctatcacttc cctgcgcaag ccgcgctgcg cgaagccatc    6360
atcgacgaag aagtcaccga gttcgccatt gcgcagcctt ccgaggcgtg gtggatcccc    6420
gccggcgagc ccatccacta cgaatacctg tatcagcgca cgccgctgaa cgaagtggcg    6480
ctggcgcata cgccgctcac gctgcgcagc cgcaacgggc tgcacgtggc gctgcacgaa    6540
gccgcgttgg tggactacgc cggcatgtgg ctgcgccgta ccgaagggca gcggctgcgt    6600
gcccacctct cgcccgccgc cgagggttgg aaggtacgcc gcaccctgcc cttcgatacc    6660
ccgtggcgca cgctgcagat cgccgatcag gccaccggcc tggttgaatc caacctcatt    6720
ctcaacctca acgaaccaaa cgccctgggc gatgtgagct gggtcaaacc gtccaaatat    6780
gtcggcgtgt ggtggtcgat gcatctcaac cagcagacct gggccaccgg cccgaaacat    6840
gcggctacca ccgccacgac caaacgctac atcgacttcg ccgccgcgca cggctttcgc    6900
ggtgtgctgg tggaaggctg gaatcccggc tgggacggcg agtggtttgg caatggcggc    6960
agcttcgatt tcaccagagc aacgccagat ttcgacctgc ctgcgctgag tagctatgcc    7020
gccggcaagg gcgtgcatct gatcggccat catgaaacgg ggtgtgcggt ggaccattac    7080
gaagatcaga ttgccgaagc gatggatctg tacgcccgtt tcggcgtgga ttcggtcaag    7140
accggctatg tctgcgacga cggccaggtg gagcggcgca atccggccgg tggcacgccg    7200
```

```
ttgcgcgaat ggcacgacgg tcagtggatg gcgcgccatc acctgcacgt ggtgcaggag      7260
gcagccgagc gccaccttgc agtcaatgcg cacgagccga tcaaggacac cggcctgcgc      7320
cgcacctatc ccaactggat ttcgcgcgaa ggcgcgcgtg gcatggaata caacgcctgg      7380
ggccagccgc ccaatccgcc cgaacacgaa gtcaacctgg tgttcactcg cctgctcgcc      7440
gggccgatgg attacacgcc cggcatcgtc agcctcaagg gccgcaatgg ccaggcgatt      7500
cccagcacgc tggcacgcca gctggctttg tacgtgacgc tctacagccc gatccagatg      7560
gcggccgatc tgcccgagca ttatctgcag caccgcgatg cgttccgttt cattgaggat      7620
gtggccgtgg actgggacca gacccgcgcg ttgaatggcg aggtgggcga ctacgtcacc      7680
attgcgcgca aggaccggca tagccgcgac tggttcctgg gcagcatcac cgacgaaatg      7740
gccgcctgtt gcaggtgccg ctggggtttc tggaaccggg cgtgcgctat cgcgcgcaga      7800
tctaccgcga tggcgatgac gccggctacg tgcacaaccc gttcgccttt atccgcgaag      7860
aacgccaggt cagcagcatc gacacgctgg aactgcggct ggcacccggt ggtggccagg      7920
cgattcgctt cgtgccgatg gagtcagcgc cctaaaagct tgcggccgca ctcgagcacc      7980
accaccacca ccactgagat ccggctgcta acaaagcccg aaaggaagct gagttggctg      8040
ctgccaccgc tgagcaataa ctagcataac cccttggggc ctctaaacgg gtcttgaggg      8100
gttttttgct gaaaggagga actatatccg ga                                    8132

<210> SEQ ID NO 3
<211> LENGTH: 25
<212> TYPE: DNA
<213> ORGANISM: artificial sequence
<220> FEATURE:
<223> OTHER INFORMATION: Int F primer for PCR
<220> FEATURE:
<221> NAME/KEY: restriction_site
<222> LOCATION: (4)..(9)
<223> OTHER INFORMATION: recognized by EcoRI

<400> SEQUENCE: 3
ccggaattca tggtgcgcga gtccg                                            25

<210> SEQ ID NO 4
<211> LENGTH: 34
<212> TYPE: DNA
<213> ORGANISM: artificial sequence
<220> FEATURE:
<223> OTHER INFORMATION: Int-EGFP R primer for PCR

<400> SEQUENCE: 4
cgcccttgct caccatgttg tgtacaatga tgtc                                  34

<210> SEQ ID NO 5
<211> LENGTH: 34
<212> TYPE: DNA
<213> ORGANISM: artificial sequence
<220> FEATURE:
<223> OTHER INFORMATION: Int-EGFP F primer for PCR

<400> SEQUENCE: 5
gacatcattg tacacaacat ggtgagcaag ggcg                                  34

<210> SEQ ID NO 6
<211> LENGTH: 27
<212> TYPE: DNA
<213> ORGANISM: artificial sequence
<220> FEATURE:
<223> OTHER INFORMATION: EGFP R primer for PCR
```

```
<220> FEATURE:
<221> NAME/KEY: restriction_site
<222> LOCATION: (4)..(9)
<223> OTHER INFORMATION: recognized by XhoI

<400> SEQUENCE: 6
ccgctcgagt tacttgtaca gctcgtc                                              27

<210> SEQ ID NO 7
<211> LENGTH: 1218
<212> TYPE: DNA
<213> ORGANISM: artificial sequence
<220> FEATURE:
<223> OTHER INFORMATION: dnaB-egfp fusion gene
<220> FEATURE:
<221> NAME/KEY: restriction_site
<222> LOCATION: (4)..(9)
<223> OTHER INFORMATION: recognized by EcoRI
<220> FEATURE:
<221> NAME/KEY: Ssp dnaB gene
<222> LOCATION: (10)..(489)
<220> FEATURE:
<221> NAME/KEY: egfp gene
<222> LOCATION: (490)..(1209)
<220> FEATURE:
<221> NAME/KEY: restriction_site
<222> LOCATION: (1210)..(1215)
<223> OTHER INFORMATION: recognized by XhoI

<400> SEQUENCE: 7
ccggaattca tggtgcgcga gtccggagct atctctggcg atagtctgat cagcctggct          60
agcacaggaa aaagagtttc tattaaagat ttgttagatg aaaaagattt tgaaatatgg         120
gcaattaatg aacagacgat gaagctggaa tcagctaaag ttagtcgtgt attttgtact         180
ggcaaaaagc tagtttatat tctaaaaact cgactaggta aactatcaa ggcaacagca          240 aatcatagat ttttaactat tgatggttgg aaaagattag atgagctatc tttaaaagag         300
catattgctc taccccgtaa actagaaagc tcctctttac aattgtcacc agaaatagaa         360
aagttgtctc agagtgatat ttactgggac tccatcgttt ctattacgga gactggagtc         420
gaagaggttt ttgatttgac tgcgccagga ccacataact tgtcgcgaa tgacatcatt          480 gtacacaaca tggtgagcaa gggcgaggag ctgttcaccg gggtggtgcc catcctggtc         540
gagctggacg gcgacgtaaa cggccacaag ttcagcgtgt ccggcgaggg cgagggcgat         600
gccacctacg gcaagctgac cctgaagttc atctgcacca ccggcaagct gcccgtgccc         660
tggcccaccc tcgtgaccac cctgacctac ggcgtgcagt gcttcagccg ctaccccgac         720
cacatgaagc agcacgactt cttcaagtcc gccatgcccg aaggctacgt ccaggagcgc         780
accatcttct tcaaggacga cggcaactac aagacccgcg ccgaggtgaa gttcgagggc         840
gacaccctgg tgaaccgcat cgagctgaag ggcatcgact tcaaggagga cggcaacatc         900
ctggggcaca agctggagta caactacaac agccacaacg tctatatcat ggccgacaag         960
cagaagaacg gcatcaaggt gaacttcaag atccgccaca acatcgagga cggcagcgtg        1020
cagctcgccg accactacca gcagaacacc cccatcggcg acggccccgt gctgctgccc        1080
gacaaccact acctgagcac ccagtccgcc ctgagcaaag accccaacga gaagcgcgat        1140
cacatggtcc tgctggagtt cgtgaccgcc gccgggatca ctctcggcat ggacgagctg        1200
tacaagtaac tcgagcgg                                                      1218

<210> SEQ ID NO 8
<211> LENGTH: 25
<212> TYPE: DNA
```

```
<213> ORGANISM: Artificial Sequence
<220> FEATURE:
<223> OTHER INFORMATION: pTWIN1 INT F primer for PCR
<220> FEATURE:
<221> NAME/KEY: restriction_site
<222> LOCATION: (4)..(9)
<223> OTHER INFORMATION: recognized by EcoRI

<400> SEQUENCE: 8
ccggaattcc tgcgcgagtc cggag                                       25

<210> SEQ ID NO 9
<211> LENGTH: 26
<212> TYPE: DNA
<213> ORGANISM: Artificial Sequence
<220> FEATURE:
<223> OTHER INFORMATION: pTWIN1 INT R primer for PCR
<220> FEATURE:
<221> NAME/KEY: restriction_site
<222> LOCATION: (4)..(9)
<223> OTHER INFORMATION: recognized by EagI

<400> SEQUENCE: 9
ccgcggccgt tgtgtacaat gatgtc                                      26

<210> SEQ ID NO 10
<211> LENGTH: 31
<212> TYPE: DNA
<213> ORGANISM: Artificial Sequence
<220> FEATURE:
<223> OTHER INFORMATION: Dht F primer for PCR
<220> FEATURE:
<221> NAME/KEY: restriction_site
<222> LOCATION: (4)..(9)
<223> OTHER INFORMATION: recognized by EagI

<400> SEQUENCE: 10
ccgcggccgg gcgatgaaaa aatggattcg c                                31

<210> SEQ ID NO 11
<211> LENGTH: 25
<212> TYPE: DNA
<213> ORGANISM: Artificial Sequence
<220> FEATURE:
<223> OTHER INFORMATION: Dht R primer for PCR
<220> FEATURE:
<221> NAME/KEY: restriction_site
<222> LOCATION: (4)..(9)
<223> OTHER INFORMATION: recognized by XhoI

<400> SEQUENCE: 11
ccgctcgagt ggtctggcaa acgtc                                       25
```

EXPRESSION CASSETTE, RECOMBINANT HOST CELL AND PROCESS FOR PRODUCING A TARGET PROTEIN

CROSS-REFERENCE TO RELATED APPLICATION

This application claims priority to Taiwanese Application No. 099137264, filed Oct. 29, 2010, the disclosure of which is incorporated herein by reference.

BACKGROUND OF THE INVENTION

1. Field of the Invention

This invention relates to an expression cassette, a recombinant host cell and a process for producing a target protein, in which a recombinant polynucleotide is constructed to encode a fusion protein comprising: (i) an anchoring protein that comprises a N-terminal amino acid sequence of an ice nucleation protein, so that the fusion protein, once expressed in a host cell, is directed by the anchoring protein to be anchored and exposed on the outer membrane of the host cell; (ii) the target protein; and (iii) a self-splicing protein that comprises a first end fused with the anchoring protein and a second end fused with the target protein, wherein the self-splicing protein comprises a N-terminal or C-terminal amino acid sequence of an intein protein at the second end thereof, such that upon an environmental stimulus, the self-splicing protein exerts a self-cleavage at the second end thereof to release the target protein from the fusion protein. The released fusion protein can then be easily recovered by a simple separating treatment such as centrifugation.

2. Description of the Related Art

With the rapid development of biotechnology, the targets of many researches in the field of life science have changed from genes to proteins, and the techniques for protein isolation and purification have attracted great attention from investigators worldwide. Recently, many techniques have been developed to isolate and purify proteins. However, not a few factors, for example the diversity of protein sources (e.g., microbial fermented broths, plant cells, animal cells, urines and bloods), the low concentrations of proteins, and the impurities contained in protein samples, increase the difficulty and complexity of protein isolation and purification. In particular, production of protein in large quantities is usually expensive due to the elaborate procedures and the specialized equipment required for cell disruption, repetitive solid-liquid phase separation, possible column purification involvement, and concentration.

In current protein engineering methods, an effective way to simplify the purification procedure is to produce a fusion protein in which an affinity tag is added to the N- or C-terminus of a target protein of interest (M. T. Hearn and D. Acosta (2001), *J. Mol. Recognit.,* 14:323-369). These kinds of tags can be glutathione S-transferase (GST), maltose-binding protein (MBP), polyhistidine, streptavidin, chitin-binding domain, or a combination thereof. Such tagged-fusion proteins can be recovered by affinity chromatography. The affinity purification procedures specifically designed for the fusion protein tags have been well established in literature (C. Mateo et al. (2001), *J. Chromatogr. A,* 915:97-106; K. Sakhamuru et al. (2000), *Biotechnol. Prog.,* 16:296-298). However, affinity columns used in affinity purification procedures of proteins are comparatively expensive and only available for small scale production. In addition, in cases of therapeutic protein, tags need to be removed from the fusion proteins. To achieve this, a protease cleavage site such as a factor Xa cleavage site, a tobacco etch virus (TEV) site, etc., was built in the fusion between the tag and the target protein (V. Schauer-Vukasinovic et al. (2002), *Anal. Bioanal. Chem.,* 373:501-507), and a site-specific protease such as the factor Xa protease or the TEV protease, etc., was required to effect a splicing at the protease cleavage site so as to release the target protein (T. D. Parks et al. (1994), *Anal. Biochem.,* 216:413-417). These site-specific proteases, however, are costly and removal of the same involves complicated procedures. Accordingly, lowering the production cost, simplifying the manufacturing procedures while increasing the yield of recombinant proteins, etc., have become the main goals of researchers in the biotech industry.

In the last decade, several self-cleaving protein modules have been developed and combined with conventional affinity tags to create new and simple affinity purification methods. In particular, a number of engineered self-cleaving inteins have been successfully used in bioseparation processes. In practice, the self-cleaving reaction can be induced at the intein's N-terminus by thiol addition or its C-terminus by a mild pH shift. The pTWIN vectors and the IMPACT™ system from New England Biolabs are the most published commercial intein systems to date, and are often paired with a chitin-binding domain as the affinity tag. A majority of the NEB systems are based on thiol-induced inteins, which can be induced by compounds including 2-mercaptoethane sulfonic acid (MESNA), hydroxylamine, thiophenol, β-mercaptoethanol, 1,4-dithiothreitol (DTT) or free cysteine. Typically, 15-30 mM DTT addition is used to trigger the cleaving reaction for N-terminally cleaving inteins. This concentration of DTT will generally reduce disulfide bonds in proteins containing them, effectively inactivating those targets. Other compounds such as MESNA, hydroxylamine or free cysteine can also be used as cleaving triggers, but they tend to leave modifications at the C-terminus of the target protein, which could affect product activity in some cases. Therefore, for disulfide-bond-containing protein targets, the thiol-induced inteins are not ideal unless the target protein can maintain activity after thiol treatment and extra modifications at the C-terminus can be tolerated (Wan-Yi Wu et al. (2011), *Protein Expression and Purification,* 76:221-228).

An efficient C-terminal cleaving intein is the ΔI-CM intein derived from the *Mycobacterium tuberculosis* recA intein. It is 18 kDa in size, and has been paired with conventional affinity tags as well as non-chromatographic purification tags. Compared to the DTT-induced inteins, the cleaving activity of the ΔI-CM intein is induced by a mild pH change from pH 8.5 to pH 6.0-6.5, suggesting its compatibility with disulfide-bonded targets. The ΔI-CM intein is also temperature dependent, allowing the purification conditions to be adjusted according to the needs of each specific target (Wan-Yi Wu et al. (2011), supra).

The IMPACT™ system from New England Biolabs is not ideal for industrial use since it requires the use of a costly chitin column, which is unsuitable for the large scale production of target proteins.

Amongst various techniques for protein isolation and purification known in the art, microbial surface display systems, which could lower production cost and simplify manufacturing procedure, have been considered to have potential for use in protein engineering. Generally, the microbial surface display system is composed of a carrier protein (also called anchoring motif), a passenger protein (i.e., the target protein), and the host cell. The carrier proteins normally are cell surface proteins associated with signal transduction, surface adherence, cell-cell recognition and immunoreaction, and those for ion channels for molecule transport. Commonly used carrier proteins include bacterial fimbriae, S-layer proteins, ice nucleation protein (INP), and outer membrane proteins (Sang Yup Lee et al. (2003), *TRENDS in Biotechnology*, 21:45-52; Po-Hung Wu et al. (2006), *Biotechnology and Bioengineering*, 95:1138-1147). Target protein can be fused with the carrier protein via N-terminal fusion, C-terminal fusion or sandwich fusion to the form a fusion protein, which, once expressed, can be displayed on the host cells' surface.

For example, US 2005/0015830 A1 discloses a process of producing a protein or polypeptide of interest in a plant or in plant cells, comprising: (i) transforming or transfecting a plant of plant cells with a nucleotide sequence having a coding region encoding a fusion protein comprising the protein or polypeptide of interest, a signal peptide functional for targeting said fusion protein to the apoplast, and a polypeptide capable of binding the fusion protein to a cell wall component, (ii) enriching cell wall components having expressed and bound fusion protein, and (iii) separating the protein or polypeptide of interest or a protein comprising the protein or polypeptide interest. Particularly, the protein or polypeptide of interest may contain one or more affinity peptide tags, such as an intein or part thereof. According to US 2005/0015830 A1, step (iii) involves cleavage of at least one peptide bond. Therefore, said fusion protein may further comprise a cleavage sequence allowing cleavage of the fusion protein, wherein the cleavage of the fusion protein may be achieved by intein-mediated cleavage. However, it is somewhat difficult to culture plant cells as compared to microbial cells. In addition, an enriching step is required so as to increase the concentration of cell wall components having expressed and bound fusion protein. Besides, the product obtained from the separating step contains not only the purified protein or polypeptide of interest but also other protein components such as signal peptide. Therefore, US 2005/0015830 A1 fails to provide a rapid and cost-efficient technique for the production of target proteins.

TW I304810 discloses an oil body-based purification method for proteins, comprising the steps of: (a) preparing a polypeptide comprising oil body-binding oleosin, an intein connected to the oleosin and a target protein connected to the intein, wherein the intein is Mxe GyrA or Ssp DnaB; (b) mixing the polypeptide with oil body so as to form an oil body mixture; (c) separating the oil body mixture from the extracted cell debris; (d) cleaving the polypeptide from the oil body mixture; and (e) separating the polypeptide from the rest of the oil body mixture. According to TW I304810, the oleosin acts as a carrier protein and the intein is Mxe GyrA or Ssp DnaB. However, liquid oil must be used in the mixing and separating steps, which inevitably increases process complexity and manufacturing cost.

Ice nucleation protein (INP) is an outer membrane protein (OMP) found in several plant pathogenic bacteria, namely *Pseudomonas* (e.g., *Pseudomonas syringae*, *Pseudomonas borealis*, *Pseudomonas putida*), *Xanthomonas* (e.g., *Xanthomonas campestris*) and *Erwinia* (e.g., *Erwinia herbicola*). INP enables the bacteria to survive freezing through formation of ice on the surface of the bacteria (L. Li et al. (2004), *Biotechnol. Bioeng.*, 85:214-221). INP has several unique structural and functional features that make it highly suitable for use in a bacterial surface display system. The specific amino acids of the N-terminal domain are relatively hydrophobic and link the protein to the outer membrane via a glycosylphosphatidyl inositol anchor. The C-terminal domain of the protein is highly hydrophilic and exposed to the medium. The central part of INP comprises a series of repeating domains that act as templates for ice crystal formation. It has been shown that full-length INP and various truncates that lack the central repeating domain yield stable surface display. This indicates that the central repeating domains are not required for export to the cell surface, and are therefore, ideal spacer units to control the distance between the passenger protein and the cell surface. A derivative that comprises the N- and C-terminal domains of INP is commonly used for surface display. However, the N-terminal domain appears to be the only prerequisite for successful targeting and surface-anchoring. Importantly, INP can be expressed at the cell surface of *E. coli* at a very high level, without affecting cell viability (Edwin van Bloois et al., *Trends in Biotechnology*, February 2011, Vol. 29, No. 2, pp. 79-86). By fusing various target proteins to the C-terminus of INP, it was found that the engineered host cell had the surface-localized activities of the target proteins (R. Freudl et al. (1986), *J. Mol. Biol.*, 188:491-494; A. Charbit et al. (1986), *EMBO J.*, 5:3029-3037; H. C. Jung et al. (1998), *Enzyme Microb. Technol.*, 22:348-354; E. J. Kim et al. (1999), Lett. Appl. Microbiol., 29:292-297; W. Bae et al. (2002), *J. Inorg. Biochem.*, 88:223-227; P. H. Wu et al. (2006), *Biotechnol. Bioeng.*, 95:1138-1147). INP has also been used in the microbial cell surface display of levansucrase, carboxymethylcellulase (CMCase), salmobin and organophosphorus hydrolase (OPH) (Sang Yup Lee et al. (2003), *TRENDS in Biotechnology*, 21:45-52; Po-Hung Wu et al. (2006), Biotechnology and Bioengineering, 95:1138-1147).

In order to develop a new rapid and cost-efficient technique for the massive production of target proteins by recombinant technology, the applicants attempted to create an expression system for target protein in fusion protein form, in which INP is used as a carrier protein for anchoring on the host cell's surface, and intein is used as an intramolecular cleavage site for releasing the target protein, such that the target protein can be easily recovered by a simple separating treatment such as centrifugation.

SUMMARY OF THE INVENTION

Therefore, this invention provides an expression cassette containing a recombinant polynucleotide encoding a fusion protein, wherein the fusion protein comprises:
(i) an anchoring protein that comprises a N-terminal amino acid sequence of an ice nucleation protein, so that the fusion protein, once expressed in a host cell transformed by the expression cassette, is directed by the anchoring protein to be anchored and exposed on the outer membrane of the host cell;
(ii) the target protein; and
(iii) a self-splicing protein that comprises a first end fused with the anchoring protein and a second end fused with the target protein, wherein the self-splicing protein comprises a N-terminal or C-terminal amino acid sequence of an intein protein at the second end thereof, such that upon an environmental stimulus, the self-splicing protein exerts a self-cleavage at the second end thereof to release the target protein from the fusion protein.

According to a second aspect, this invention provides a recombinant vector comprising the aforesaid expression cassette.

According to a third aspect, this invention provides a recombinant host cell which contains the aforesaid recombinant vector.

According to a fourth aspect, this invention provides a process for producing a target protein, comprising:
providing a host cell having an outer membrane and harboring an expression cassette containing a recombinant polynucleotide therein, wherein the host cell is capable of expressing a fusion protein encoded by the recombinant polynucleotide and wherein the fusion protein comprises:
  (i) an anchoring protein that comprises a N-terminal amino acid sequence of an ice nucleation protein, so that the fusion protein, once expressed in the host cell, is directed by the anchoring protein to be anchored and exposed on the outer membrane of the host cell;
  (ii) the target protein; and
  (iii) a self-splicing protein that comprises a first end fused with the anchoring protein and a second end fused with the target protein, wherein the self-splicing protein comprises a N-terminal or C-terminal amino acid sequence of an intein protein at the second end thereof, such that upon an environmental stimulus, the self-splicing protein exerts a self-cleavage at the second end thereof to release the target protein from the fusion protein;

obtaining a cell culture by culturing the host cell in a medium under a condition that enables the fusion protein to be expressed and anchored on the outer membrane of the host cell;

subjecting the cell culture thus obtained to an environmental stimulus that induces the self-splicing protein to exert a self-cleavage at the second end thereof; and harvesting the target protein by a separating treatment.

BRIEF DESCRIPTION OF THE DRAWINGS

The above and other objects, features and advantages of this invention will become apparent with reference to the following detailed description and the preferred embodiments taken in conjunction with the accompanying drawings, in which.

DETAILED DESCRIPTION OF THE INVENTION

Figure 1:
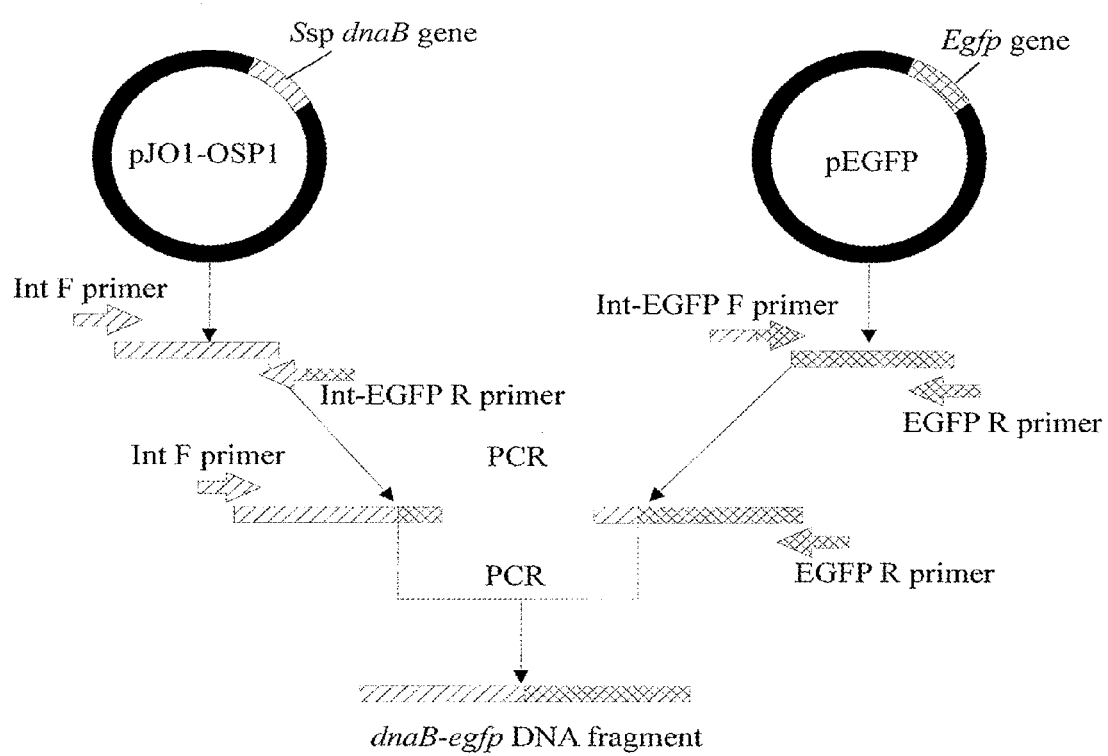
FIG. 1 schematically shows the generation of a dnaB-egfp DNA fragment by PCR reactions, said dnaB-egfp DNA containing in sequence along a transcription direction an intact Synechocystis sp dnaB gene (Ssp dnaB gene) fused with an intact enhanced green fluorescent protein gene (egfp gene)

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless defined otherwise, all technical and scientific terms used herein have the meaning commonly understood by a person skilled in the art to which this invention belongs. One skilled in the art will recognize many methods and materials similar or equivalent to those described herein, which could be used in the practice of the present invention. Indeed, the present invention is in no way limited to the methods and materials described.

"Recombinant DNA technology" refers to techniques for uniting two heterologous DNA molecules, usually as a result of in vitro ligation of DNAs from different organisms. Recombinant DNA molecules are commonly produced by experiments in genetic engineering. Synonymous terms include "gene splicing," "molecular cloning" and "genetic engineering." The product of these manipulations results in a "recombinant" or "recombinant molecule."

Techniques for manipulating nucleic acids, such as those for generating mutation in sequences, subcloning, labeling, probing, sequencing, hybridization and so forth, are described in detail in scientific publications and patent documents. See, for example, Sambrook J, Russell D W (2001) Molecular Cloning: a Laboratory Manual, 3rd ed. Cold Spring Harbor Laboratory Press, New York; Current Protocols in Molecular Biology, Ausubel ed., John Wiley & Sons, Inc., New York (1997); Laboratory Techniques in Biochemistry and Molecular Biology Hybridization With Nucleic Acid Probes, Part I, Theory and Nucleic Acid Preparation, Tijssen ed., Elsevier, N.Y. (1993).

As used herein, the term "expression cassette" refers to a construct of genetic material that contains coding sequences and enough regulatory information to direct proper transcription and translation of the coding sequences in a recipient cell. The expression cassette may be inserted into a vector for targeting to a desired host cell and/or into a subject.

As used herein, the term "polynucleotide" refers to a sequence of nucleotides connected by phosphodiester linkages. A polynucleotide of this invention can be a deoxyribonucleic acid (DNA) molecule or ribonucleic acid (RNA) molecule in either single- or double-stranded form. Nucleotide bases are indicated herein by a single letter code: adenine (A), guanine (G), thymine (T), cytosine (C), inosine (I) and uracil (U). A polynucleotide of this invention can be prepared using standard techniques well known to one of ordinary skill in the art. This term is not to be construed as limiting with respect to the length of a polymer, and encompasses known analogues of natural nucleotides, as well as nucleotides that are modified in the sugar and/or phosphate moieties. This term also encompasses nucleic acids containing modified backbone residues or linkages, which are synthetic, naturally occurring, and non-naturally occurring, which have similar binding properties as the reference nucleic acid, and which are metabolized in a manner similar to the reference nucleotides.

As used herein, the term "DNA fragment" refers to a DNA polymer, in the form of a separate segment or as a component of a larger DNA construct, which has been derived either from isolated DNA or synthesized chemically or enzymatically such as by methods disclosed elsewhere.

The terms "nucleic acid" and "nucleic acid sequence" as used herein refer to a deoxyribonucleotide or ribonucleotide sequence in single-stranded or double-stranded form, that comprises naturally occurring and known nucleotides or artificial chemical mimics. The term "nucleic acid" as used herein is interchangeable with the terms "gene," "cDNA," "mRNA," "oligo-nucleotide" and "polynucleotide" in use.

As used herein, the term "gene" refers to a DNA sequence, including but not limited to a DNA sequence that can be transcribed into mRNA which can be translated into polypeptide chains, transcribed into rRNA or tRNA, or serve as recognition sites for enzymes and other proteins involved in DNA replication, transcription and regulation. This definition includes various sequence polymorphisms, mutations, and/or sequence variants wherein such alterations do not affect the function of the gene product. The term "gene" is intended to include not only regions encoding gene products but also regulatory regions including, e.g., promoters, termination regions, translational regulatory sequences (such as ribosome binding sites and internal ribosome entry sites), enhancers, silencers, insulators, boundary elements, replication origins, matrix attachment sites, and locus control regions. The term "gene" further includes all introns and other DNA sequences spliced from the mRNA transcript, along with variants resulting from alternative splice sites. The term "gene" includes, but is not limited to, structural genes, immunity genes and secretory (transport) genes.

As used herein, the term "fusion gene" refers to a DNA fragment in which two or more genes are fused in a single reading frame to encode two or more proteins that are fused together via one or more peptide bonds. As used herein, the term "fusion protein" refers to a protein or polypeptide encoded by a fusion gene and it may be used interchangeably with the term "fusion gene product."

As used herein, the term "coding region" refers to a nucleic acid sequence encoding an amino acid that is found in a nascent polypeptide translated from a mRNA molecule.

As used herein, the term "promoter" can be used interchangeably with the term "promoter sequence" and refers to a DNA regulatory region capable of binding RNA polymerase in a cell and initiating transcription of a downstream (3' direction) coding sequence. The promoter is bound at its 3' terminus by the translation start codon of a coding sequence and extends upstream (5' direction) to include a minimum number of bases or elements necessary to initiate transcription. Promoters which cause a gene to be expressed in most cell types at most times are commonly referred to as "constitutive promoters". Promoters which cause conditional expression of a structural nucleotide sequence under the influence of changing environmental conditions or developmental conditions are commonly referred to as "inducible promoter."

The term "operatively connected" as used herein means that a first sequence is disposed sufficiently close to a second sequence such that the first sequence can influence the second sequence or regions under the control of the second sequence. For instance, a promoter sequence may be operatively connected to a gene sequence, and is normally located at the 5'-terminus of the gene sequence such that the expression of the gene sequence is under the control of the promoter sequence. In addition, a regulatory sequence may be operatively connected to a promoter sequence so as to enhance the ability of the promoter sequence in promoting transcription. In such case, the regulatory sequence is generally located at the 5'-terminus of the promoter sequence.

As used herein, the term "upstream" and "downstream" refer to the position of an element of nucleotide sequence. "Upstream" signifies an element that is more 5' than the reference element. "Downstream" signifies an element that is more 3' than the reference element.

The term "expression vector" as used herein refers to any recombinant expression system capable of expressing a selected nucleic acid sequence, in any host cell in vitro or in vivo, constitutively or inducibly. The expression vector may be an expression system in linear or circular form, and covers expression systems that remain episomal or that integrate into the host cell genome. The expression system may or may not have the ability to self-replicate, and it may drive only transient expression in a host cell.

According to this invention, the term "transformation" can be used interchangeably with the term "transfection" when such term is used to refer to the introduction of an exogenous nucleic acid molecule into a selected host cell. According to techniques known in the art, a nucleic acid molecule (e.g., a recombinant DNA construct or a recombinant vector) can be introduced into a selected host cell by various techniques, such as calcium phosphate- or calcium chloride-mediated transfection, electroporation, microinjection, particle bombardment, liposome-mediated transfection, transfection using bacterial bacteriaphages, transduction using retroviruses or other viruses (such as vaccinia virus or baculovirus of insect cells), protoplast fusion, *Agrobacterium*-mediated transformation, or other methods.

The terms "cell," "host cell," "transformed host cell" and "recombinant host cell" as used herein can be interchangeably used, and not only refer to specific individual cells but also include sub-cultured offsprings or potential offsprings thereof. Sub-cultured offsprings formed in subsequent generations may include specific genetic modifications due to mutation or environmental influences and, therefore, may factually not be fully identical to the parent cells from which the sub-cultured offsprings were derived. However, sub-cultured cells still fall within the coverage of the terms used herein.

The terms "polypeptide," "peptide" and "protein" as used herein can be interchangeably used, and refer to a polymer formed of amino acid residues, wherein one or more amino acid residues are naturally occurring amino acids or artificial chemical mimics.

As used herein, the term "target protein" refers to a protein of interest that is the subject to be isolated and purified.

As used herein, the term "cultivating" refers to growing or maintaining a population of cells under suitable conditions in a medium. According to this invention, the term "cultivating" may be interchangeably used with the term "cultivation" and the term "culturing."

In recent years, various inteins have been used to generate target protein from the fusion protein without the addition of protease. Intein is an autocatalytic protein splicing and cleavage element and it was first found in *Saccharomyces cerevisiae*. To date, there have been more than 100 inteins identified from eubacteria, archea and eukaryotic unicellular organisms. Intein may be fused to the N- or C-terminus of the target protein, and self-cleavage of intein from the fusion protein can occur under induction conditions (F. B. Perler et al. (1994), *Nucleic Acids Res.*, 22:1125-1127; P. Shemella et al. (2007), *Biophys. J.*, 92:847-853). However, a cell disruption process is still needed to harvest the soluble proteins from the host cell. Due to the impurity of cell protein in the supernatant, after the cell disruption, a further affinity process is still required to purify the target protein (S. Mathys et al. (1999), *Gene*, 231:1-13).

In this invention, the applicants developed a novel and yet simple protein production strategy, which utilizes an expression cassette comprising a recombinant polynucleotide encoding a fusion protein that comprises an INP protein, in particular a truncated INP portion of *Xanthomonas campestris* (P. H. Wu et al. (2006), *Biotechnol. Bioeng.*, 95:1138-1147) as an anchoring protein for anchoring the target protein on the host cell membrane, and an intein protein as a self-splicing element built between the anchoring protein and the target protein. *E. coli* was used as a model to carry the INP-INT expression cassette according to this invention and the fusion protein expressed on the bacterial surface under induction condition. The bacterial cells were harvested by centrifugation, and then re-suspended in a buffer solution. Next, by adjusting the pH value and/or temperature of the solution, the target protein was released by virtue of the self-cleavage of the intein protein, and then collected by centrifugation. With enhanced green fluorescent protein (EGFP) and D-hydantoinase as the target protein, the INP-INT expression cassette according to this invention was verified to be effective and efficient in the production of target protein in a rapid, convenient and non-expensive manner.

Accordingly, this invention provides an expression cassette containing a recombinant polynucleotide encoding a fusion protein, wherein the fusion protein comprises:
  (i) an anchoring protein that comprises a N-terminal amino acid sequence of an ice nucleation protein, so that the fusion protein, once expressed in a host cell transformed by the expression cassette, is directed by the anchoring protein to be anchored and exposed on the outer membrane of the host cell;
  (ii) the target protein; and
  (iii) a self-splicing protein that comprises a first end fused with the anchoring protein and a second end fused with the target protein, wherein the self-splicing protein comprises a N-terminal or C-terminal amino acid sequence of an intein protein at the second end thereof, such that upon an environmental stimulus, the self-splicing protein exerts a self-cleavage at the second end thereof to release the target protein from the fusion protein.

The expression cassette of this invention can be incorporated into an expression vector to form a recombinant vector, which in turn may be used to transform a competent host cell which is able to express the recombinant gene contained in the expression cassette, so that the expressed fusion protein is anchored on the host cell's surface and the target protein contained can be easily harvested by inducing the self-cleavage of the self-splicing protein contained in the expressed fusion protein.

Accordingly, this invention provides a process for producing a target protein, comprising:
  providing a host cell having an outer membrane and harboring an expression cassette containing a recombinant polynucleotide therein, wherein the host cell is capable of expressing a fusion protein encoded by the recombinant polynucleotide and wherein the fusion protein comprises:
  (i) an anchoring protein that comprises a N-terminal amino acid sequence of an ice nucleation protein, so that the fusion protein, once expressed in the host cell, is directed by the anchoring protein to be anchored and exposed on the outer membrane of the host cell;
  (ii) the target protein; and
  (iii) a self-splicing protein that comprises a first end fused with the anchoring protein and a second end fused with the target protein, wherein the self-splicing protein comprises a N-terminal or C-terminal amino acid sequence of an intein protein at the second end thereof, such that upon an environmental stimulus, the self-splicing protein exerts a self-cleavage at the second end thereof to release the target protein from the fusion protein;
  obtaining a cell culture by culturing the host cell in a medium under a condition that enables the fusion protein to be expressed and anchored on the outer membrane of the host cell;
  subjecting the cell culture thus obtained to an environmental stimulus that induces the self-splicing protein to exert a self-cleavage at the second end thereof; and
  harvesting the target protein by a separating treatment.

The term "outer membrane", as used herein, means the membrane (composed primarily of lipopolysaccharides, phospholipids, lipoprotein, and specific membrane proteins) which is farthest from the center of a host cell. According to this invention, the term "outer membrane" includes the outer membranes of prokaryotic cells, in particular gram-negative bacteria such as *E. coli*, and the cell membranes of eukaryotic cells (e.g., animal cells such as mammalian cells), on which the anchoring protein can target and be immobilized.

The ice nucleation protein in full length is known to have three domains, i.e., the N-terminal domain that is relatively hydrophobic and link the protein to the outer membrane via a glycosylphosphatidyl inositol anchor, the C-terminal domain that is highly hydrophilic and normally is exposed outside the host cell, and the internal repeating domain that contains a plurality of repeating units and can act as a spacer unit to control the distance between the passenger protein and the cell surface. Therefore, according to this invention, the anchoring protein in the fusion protein can be selected from the group consisting of a full-length ice nucleation protein and a truncated ice nucleation protein.

According to this invention, the full-length INP may be the ice nucleation proteins of *Pesudomonas* sp., e.g., *Pseudomonas syringae, Pseudomonas borealis, Pseudomonas putida*, etc., *Xanthomonas* sp., e.g., *Xanthomonas campestris*, and *Erwinia* sp., e.g., *Erwinia herbicola*. In a preferred embodiment of this invention, the full-length INP is selected from the group consisting of InaK, Ina Q, InaV and InaZ of *Pseudomonas syringae*, InaW of *Pseudomonas fluorescens*, and IceE of *Erwinia herbicola*.

According to this invention, the truncated ice nucleation protein is a truncated form of any one of the aforesaid full-length ice nucleation proteins. As compared to a corresponding full-length ice nucleation protein, the truncated ice nucleation protein is truncated at least in the internal repeating domain without impeding the function of the N-terminal amino acid sequence to anchor on the host cell's outer membrane. In a preferred embodiment of this invention, the truncated ice nucleation protein is one containing the N-terminal domain and the C-terminal domain as well as five internal repeating units. In another preferred embodiment of this invention, the truncated ice nucleation protein is one containing the N-terminal domain and two internal repeating units. In a more preferred embodiment of this invention, the truncated INP is a truncated ice nucleation protein (referred to as "INPNC" hereinafter) encoded by the inaNC gene contained in Plasmid pinaXNC1-aglA2 (Po-Hung Wu et al. (2006), *Biotechnology and Bioengineering*, 95:1138-1149). In connection with other ice nucleation proteins for use in this invention, reference is made to Edwin van Bloois et al. (2011), supra.

According to this invention, the self-splicing protein may be an intein protein selected from the group consisting of Ssp DnaB intein, Ssp DnaE intein, Mxe GyrA intein, VMA intein, Mtu RecA intein, Psp Pol-I intein, PI-pful intein, PI-pfull intein, and Mth RIR1 intein. In a preferred embodiment of this invention, the self-splicing protein is Ssp DnaB intein.

According to this invention, the expression cassette further comprises a promoter sequence operatively connected to the recombinant polynucleotide. Promoter sequences suitable for use in this invention are preferably derived from any one of the following: viruses, bacterial cells, yeast cells, fungal cells, algal cells, plant cells, insect cells, animal cells, and human cells. For example, a promoter useful in bacterial cells includes, but is not limited to, tac promoter, T7 promoter, T5 promoter, lac promoter, T7 A1 promoter, trp promoter, trc promoter, araBAD promoter, and $\lambda P_R P_L$ promoter. A promoter useful in plant cells includes, e.g., $^{35}$S CaMV promoter, actin promoter, ubiquitin promoter, etc. In a preferred embodiment of this invention, the promoter is a T7 promoter.

According to this invention, the recombinant vector may include other expression control elements, such as a transcription starting site, a transcription termination site, a ribosome binding site, a RNA splicing site, a polyadenylation site, a translation termination site, etc. Vectors suitable for use in this invention may further include additional regulatory elements, such as transcription/translation enhancer sequences, and at least a marker gene or reporter gene allowing for the screening of the vectors under suitable conditions. Marker genes suitable for use in this invention include, for instance, dihydrofolate reductase gene and G418 or neomycin resistance gene useful in eukaryotic cell cultures, and ampicillin, streptomycin, tetracycline or kanamycin resistance gene useful in *E. coli* and other bacterial cultures. Vectors suitable for use in this invention may further include a nucleic acid sequence encoding a secretion signal. These sequences are well known to those skilled in the art.

Culture media and culture conditions for host cells suitable for carrying out DNA recombination techniques are well known in the field of biotechnology. For instance, host cells may be cultured in a fermentation bioreactor, a shaking flask, a test tube, a microtiter plate, or a petri dish, and cultivation of the host cells may be conducted under conditions suitable for growth of said cells, including the culture temperature, the pH value of the culture medium, and the dissolved oxygen concentration of the culture.

According to this invention, the environmental stimulus that induces the self-cleavage of the self-splicing protein is selected from the group consisting of a pH change, a temperature change, a salt concentration, or a combination thereof. In a preferred embodiment of this invention, the environmental stimulus is a pH change, in which the cell culture is transferred from a first pH to a second pH, wherein the second pH is higher or lower than the first pH. In a more preferred embodiment of this invention, the environmental stimulus is a pH change, in which the cell culture is transferred from a first pH of ranging from 6-10 to a second pH ranging from 8-10. In a more preferred embodiment of this invention, the environmental stimulus is a pH change, in which the cell culture is transferred from pH 8.5 to pH 7.5. In another more preferred embodiment of this invention, the environmental stimulus is a pH change, in which the cell culture is transferred from pH 7 to pH 10.

In another preferred embodiment of this invention, the environmental stimulus is a temperature change, in which the cell culture is transferred from a first temperature ranging from 15° C. to 37° C. to a second temperature ranging from 18° C. to 37° C., wherein the second temperature is higher than the first temperature. In a more preferred embodiment of this invention, the environmental stimulus is a temperature change, in which the cell culture is transferred from 18° C. to 37° C.

This invention will be described in more detail with reference to the following examples, which are given for the purpose of illustration only and are not intended to limit the scope of this invention in any way.

EXAMPLES

Experimental Materials

1. LB broth was purchased from Scharlau Chemie, S.A. (Barcelona, Spain).
2. Restriction enzymes EcoRI, XhoI and EagI were purchased from New England Biolabs, Inc. (Beverly, Mass., USA).
3. Primers used in the polymerase chain reaction (PCR) experiments, infra, were synthesized by Tri-I Biotech, Inc. (New Taipei City, Taiwan).

4. The following materials were purchased from GENEMARK Technology Co., Ltd. (Tainan City, Taiwan): Gel Elution Kit (Cat. No. DP03); pOSI-T PCR Cloning kit (Cat. No. OS-01), which includes a pOSI-T vector (3,313 bps) carrying a lac promoter ($P_{lac}$) and a Kanamycin-Resistance ORF; and Plasmid Miniprep Purification Kit II (Cat. No. DP01).
5. The following materials were purchased from Epicentre Technologies Corp. (Madison, Wis., USA): T4 DNA ligase; 10× reaction buffer; and ATP solution.
6. Plasmid pJO1-OSP1 (5,297 bps, see SEQ ID NO:1), which was derived from a plasmid pTWIN1 (New England Biolabs, Beverly, Mass., USA), was kindly provided by Dr. Jason Tze-Cheng Tzen (Graduate Institute of Biotechnology, National Chung Hsing University, Taichung City, Taiwan). Plasmid pJO1-OSP1 carries a *Synechocystis* sp. dnaB gene (Ssp dnaB gene) encoding a DnaB intein.
7. Plasmid pinaXNC1-aglA2 (8,132 bps, see SEQ ID NO:2; Po-Hung Wu et al. (2006), *Biotechnology and Bioengineering*, 95:1138-1149) was kindly provided by Dr. Wen-Teng Wu (Department of Chemical Engineering, National Cheng Kung University, Tainan City, Taiwan). Plasmid pinaXNC1-aglA2 carries a truncated inaNC gene derived from the full-length in a gene of *Xanthomonas campestris* BCRC 12846 and contains restriction sites for EcoRI and XhoI. The inaNC gene encodes a truncated ice nucleation protein (referred to as "INPNC" hereinafter) that consists of the N-terminal and C-terminal domains of the ice nucleation protein of *Xanthomonas campestris* BCRC 12846.
8. Plasmid pEGFP (3,355 bps) was purchased from Clontech Laboratories, Inc. (Mountain View, Calif., USA). Plasmid pEGFP carries a lac promoter ($P_{lac}$), an enhanced green fluorescent protein (EGFP) encoding gene, an ampicillin-resistance gene ($Amp^r$), and a multiple cloning site (MCS) that includes a restriction site for EcoRI therein.
9. Plasmid pQE-bcdht was kindly provided by Dr. Wen-Hwei Hsu of Institute of Molecular Biotechnology, National Chung Hsing University, Taichung City, Taiwan. Plasmid pQE-bcdht carries a dht gene encoding D-hydantoinase (Dht).
10. *Escherichia coli* strains DH5α and DH1(DE3) were purchased from Gibco-BRL Life Technologies, Inc. (Gaithersburg, Md., USA). *Escherichia coli* strain ER2566 was purchased from New England Biolabs (Beverly, Mass., USA).

General Experimental Procedures:

Concerning the experimental methods and relevant techniques for DNA cloning as employed in this invention, such as DNA cleavage reaction by restriction enzymes, DNA ligation with T4 DNA ligase, polymerase chain reaction (PCR), agarose gel electrophoresis, sodium dodecyl sulfate-polyacrylamide gel electrophoresis (SDS-PAGE) and plasmid transformation, etc., reference is made to a textbook widely known in the art: Sambrook J, Russell D W (2001) Molecular Cloning: a Laboratory Manual, 3rd ed. Cold Spring Harbor Laboratory Press, New York. These techniques can be readily performed by those skilled in the art based on their professional knowledge and experience.

1. Preparation of Competent *E. Coli* Cells

Cells of a selected *E. coli* strain were inoculated into the LB broth and cultivated overnight at 37° C. with shaking (150 rpm). Thereafter, a 800 µL aliquot of the overnight culture was inoculated into 40 mL fresh LB broth and cultivated at 37° C. with shaking (150 rpm). Upon reaching a cell density of about 0.2~0.4 ($OD_{600}$), the resultant culture was transferred into a sterile centrifuge tube, followed by centrifugation (4° C., 5,000 rpm, 10 min). After removal of the supernatant, a 20 mL ice cold $CaCl_2$ solution (0.1 M) was added into the centrifuge tube to thoroughly suspend the bacterial cells, and the resultant bacterial cell suspension was allowed to stand on ice for 1 hr, followed by centrifugation (4° C., 5,000 rpm, 10 min). After removal of the supernatant, a 4 mL ice cold $CaCl_2$ solution (0.1 M, containing 15% glycerol) was added into the centrifuge tube to thoroughly suspend the bacterial cells, so that a suspension of $CaCl_2$-treated competent *E. coli* cells was obtained. The competent *E. coli* cell suspension was then aliquoted into microcentrifuge tubes (100 µL per tube) and stored at −80° C. until use.

2. Transformation of *E. Coli* Cells

A microcentrifuge tube as prepared in the preceding section was removed from −80° C. and allowed to stand on ice for at least 15 min, so that a 100 µL aliquot of the competent *E. coli* cell suspension stored therein was thawed. The thawed competent *E. coli* cell suspension was then evenly admixed with a selected plasmid [100 ng/10 µL], followed by standing on ice for 1 hr. The resulting mixture was then placed in a 42° C. water bath for 2 min, followed by standing on ice for 5 min. After evenly admixing with 200 µL LB broth, the resulting mixture was cultivated at 37° C. with shaking (150 rpm) for 1 hr. The bacterial culture thus obtained was plated on solid agar plates containing 50 µg/mL kanamycin and cultivated at 37° C. for 12 to 16 hrs.

Example 1

Construction of Recombinant Vector pINPNC-INT-EGFP

A. Preparation of a dnaB-egfp DNA Fragment Containing a Ssp dnaB Gene Fused with an egfp Gene The dnaB-egfp DNA fragment, which contains in sequence along a transcription direction an intact Ssp dnaB gene fused with an intact egfp gene, was obtained according to the construction scheme shown in FIG. 1 and the procedures described below.

Based on the nucleotide sequence of the Ssp dnaB gene located in the plasmid pJO1-OSP1, i.e., nucleotide residues 4578 to 5057 in SEQ ID NO:1, and the nucleotide sequence of the egfp gene located in the plasmid pEGFP, the four primers as shown in the following Table 1 were designed:

TABLE 1

Primers used in the production of the dnaB-egfp DNA fragment via PCR reaction

| Primer | Nucleotide sequence (5'→3') |
| --- | --- |
| Int F | EcoRI<br>ccg<u>gaattc</u>atggtgcgcgagtccg (SEQ ID NO: 3) |
| Int-EGFP R | cgcccttgctcaccatgttgtgtacaatgatgtc (SEQ ID NO: 4) |

TABLE 1-continued

Primers used in the production of the dnaB-egfp DNA fragment via PCR reaction

| Primer | Nucleotide sequence (5'→3') |
|---|---|
| Int-EGFP F | gacatcattgtacacaacatggtgagcaagggcg (SEQ ID NO: 5) |
| EGFP R | XhoI ccgctcgagttacttgtacagctcgtc (SEQ ID NO: 6) |

Note:
The underlined nucleotides represent the recognition site of a restriction enzyme as indicated above.

With the plasmid pJO1-OSP1 as a template, a first PCR product (505 bps) containing an intact Ssp dnaB gene fused with a partial 5'-region of the egfp gene was obtained from a PCR experiment using both the Int F primer and the Int-EGFP R primer as shown in Table 1 and the PCR conditions as shown in Table 2, followed by a 1.2% agarose gel electrophoresis for molecular weight verification, and recovery and purification using the Gel Elution Kit.

TABLE 2

PCR reaction conditions used for the amplification of the first PCR product.

| Contents | Volume (μL) |
|---|---|
| pJO1-OSP1 | 5 |
| Int F primer (2.5 mM) | 2 |
| Int-EGFP R primer (2.5 mM) | 2 |
| dNTPs (10 mM) | 0.5 |
| DNA polymerase | 0.5 |
| 10X reaction buffer | 3 |
| ddH$_2$O | 17 |

Operation conditions:
Denaturation at 95° C. for 5 minutes, followed by 30 cycles of the following reactions: denaturation at 95° C. for 1 minute, primer annealing at 52° C. for 30 seconds, and elongation at 72° C. for 2 minutes; and finally extension at 72° C. for 4 minutes.

In the meantime, with the plasmid pEGFP as a template, a second PCR product (747 bps) containing a partial 3'-region of the Ssp dnaB gene fused with an intact egfp gene was obtained from a PCR experiment using both the Int-EGFP F primer and the EGFP R primer as shown in Table 1 and the PCR conditions as shown in Table 3, followed by a 1.2% agarose gel electrophoresis for molecular weight verification, and recovery and purification using the Gel Elution Kit.

TABLE 3

PCR reaction conditions used for the amplification of the second PCR product.

| Contents | Volume (μL) |
|---|---|
| pEGFP | 5 |
| Int-EGFP F primer (2.5 mM) | 2 |
| EGFP R primer (2.5 mM) | 2 |
| dNTPs (10 mM) | 0.5 |
| DNA polymerase | 0.5 |
| 10X reaction buffer | 3 |
| ddH$_2$O | 17 |

Operation conditions:
Denaturation at 95° C. for 5 minutes, followed by 30 cycles of the following reactions: denaturation at 95° C. for 1 minute, primer annealing at 54° C. for 30 seconds, and elongation at 72° C. for 2 minutes; and finally extension at 72° C. for 7 minutes.

The first and second PCR products thus obtained were respectively dissolved in sterile ddH$_2$O [50 ng/μL] and then subjected to a PCR experiment using both the Int F primer and the EGFP R primer as shown in Table 1 and the PCR conditions as shown in Table 4, followed by a 1.2% agarose gel electrophoresis for molecular weight verification, and recovery and purification using the Gel Elution Kit, so that a third PCR product of 1,218 bps was obtained.

TABLE 4

PCR reaction conditions used for the amplification of the third PCR product.

| Contents | Volume (μL) |
|---|---|
| The first PCR product (50 ng/μL) | 2 |
| The second PCR product (50 ng/μL) | 2 |
| Int F primer (2.5 mM) | 2 |
| EGFP R (2.5 mM) | 2 |
| dNTPs (10 mM) | 0.5 |
| DNA polymerase | 0.5 |
| 10X reaction buffer | 3 |
| ddH$_2$O | 17 |

Operation conditions:
Denaturation at 95° C. for 5 minutes, followed by 30 cycles of the following reactions: denaturation at 95° C. for 1 minute, primer annealing at 52° C. for 30 seconds, and elongation at 72° C. for 2 minutes; and finally extension at 72° C. for 7 minutes.

According to the primer design shown in Table 1, the third PCR product thus obtained contained in sequence along a transcription direction an intact Ssp dnaB gene fused with an intact egfp gene, in which an EcoRI site (gaattc) is located upstream of the Ssp dnaB gene and a XhoI site (ctcgag) is located downstream of the egfp gene.

B. Construction of Recombinant Plasmid pT-INT-EGFP Carrying the dnaB-egfp DNA Fragment The third PCR product as obtained in the preceding section was cloned into a pOSI-T vector using a pOSI-T PCR Cloning kit according to the manufacturer's instructions, and the recombinant plasmid thus formed was transformed into competent E. coli DH5α cells according to the procedures as described in the General Experimental Procedures. Thereafter, a kanamycin-resistant colony grown on the solid agar plate was taken by a platinum loop and inoculated into the LB broth containing 50 μg/mL kanamycin. After cultivation at 37° C. for 16 hrs, a portion of the bacterial culture was subjected to plasmid recovery using the Plasmid Miniprep Purification Kit II. The recovered plasmid was verified to generate a PCR product of 1218 bps after subjecting to a PCR experiment using both the Int F primer and the EGFP R primer as shown in Table 1 and the PCR conditions as shown in Table 4, followed by a 1.2% agarose gel electrophoresis. According to a sequencing analysis conducted by Tri-I Biotech, Inc., the recovered plasmid was determined to carry a dnaB-egfp fusion gene and have a nucleotide sequence as shown in SEQ ID NO:7. This recombinant plasmid was named "pT-INT-EGFP" and the E. coli transformant harboring the same was designated as "E. coli DH5α/pT-INT-EGFP."

C. Construction of Recombinant Plasmid pINPNC-INT-EGFP

The recombinant plasmid pT-INT-EGFP as obtained in the preceding section B was cleaved with restriction enzymes EcoRI and XhoI so that a first cleavage product (1,206 bps) containing the dnaB-egfp fusion gene was obtained. In the meantime, plasmid plnaXNC-aglA2 was cleaved with restriction enzymes EcoRI and XhoI so that a second cleavage product (6,033 bps) containing the inaNC gene was obtained. After placing the first and second cleavage products into a microcentrifuge tube in a molar ratio of 1:1, 0.5 µL of T4 DNA ligase (2 U/µL), 2 µL of 10× reaction buffer and 0.5 µL of 25 mM ATP solution were added into the microcentrifuge tube with gentle mixing, followed by addition of sterile ddH$_2$O until a total volume of 20 µL was reached. Ligation of the first and second cleavage products was effected by placing the microcentrifuge tube at 16° C. for 16 hrs, followed by standing in a 70° C. dry bath for 5-10 min.

Figure 2:
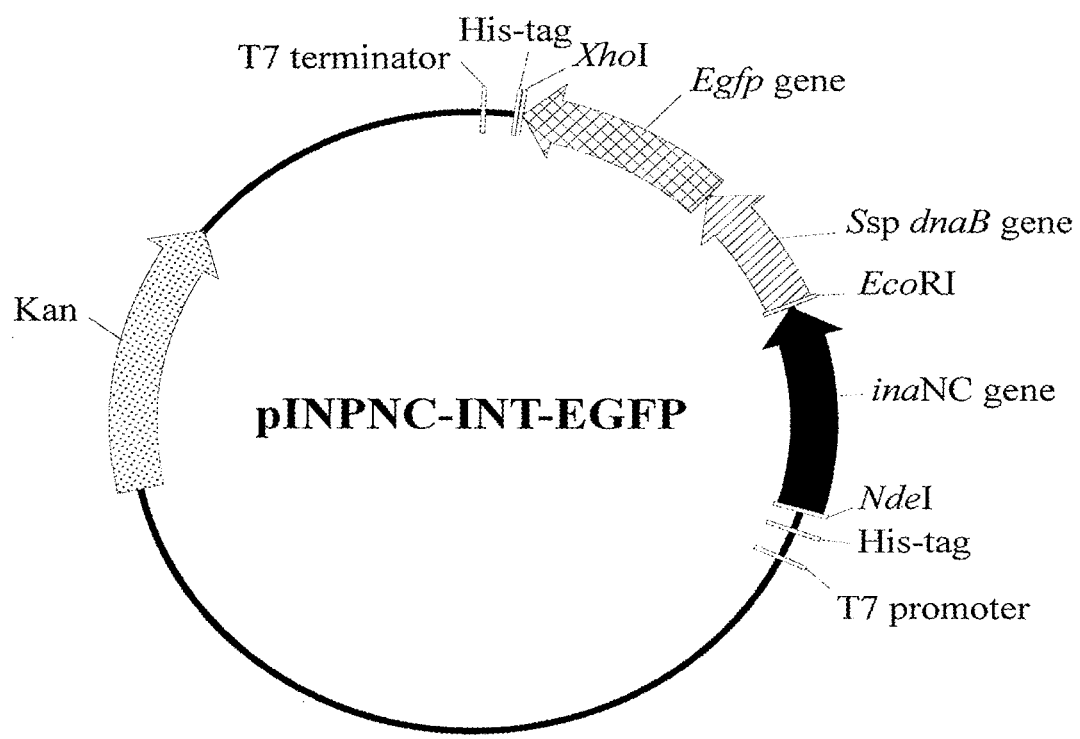
FIG. 2 shows the construct of recombinant plasmid pINPNC-INT-EGFP, which carries a fusion gene consisting of a truncated inaNC gene, the Ssp dnaB gene and the egfp gene along the transcription direction; in which Kan represents kanamycin resistance gene; and NdeI, EcoRI and XhoI represent the recognition sites of the corresponding restriction enzymes, respectively.

The ligated product thus obtained was subsequently transformed into competent *E. coli* DH1(DE3) cells according to the procedures as described in the General Experimental Procedures. An *E. coli* transformant thus obtained was designated as "*E. coli* DH1(DE3)/pINPNC-INT-EGFP," which was verified to harbor a recombinant plasmid named "pINPNC-INT-EGFP," which according to a sequencing analysis conducted by Tri-I Biotech, Inc., was determined to have a plasmid construct as shown in FIG. 2.

Example 2

Production of Enhanced Green Fluorescent Protein (EGFP) from Fusion Protein INPNC-INT-EGFP Expressed by *E. coli* DH1(DE3)/pINPNC-INT-EGFP Experimental Procedures:
A. Production of Fusion Protein INPNC-INT-EGFP in Cells of *E. coli* DH1(DE3)/pINPNC-INT-EGFP by isopropyl-β-D-thiogalactopyranoside (IPTG) Induction The cells of *E. coli* transformant DH1(DE3)/pINPNC-INT-EGFP as obtained in Example 1 were inoculated into 40 mL of the LB broth containing 50 µg/mL kanamycin and cultivated at 37° C. with shaking (150 rpm). After reaching a cell density of about 1 (OD$_{600}$), the bacterial culture was added with IPTG to a final concentration of 1 mM, and then cultivated at 18° C. (to prevent protein aggregation) with shaking (150 rpm) for further 24 hrs, so as to induce the bacterial cells to express the fusion protein INPNC-INT-EGFP. Bacterial culture without IPTG induction was used as a control.

Thereafter, a few drops of the bacterial culture with or without IPTG induction was added onto a slide and covered with a cover slip, followed by examination using a fluorescent microscope (Nikon, TE 2000-S) at an excitation wavelength of 488 nm and an emission wavelength of 510 nm, so as to determine whether or not the cultured cells expressed the fusion protein INPNC-INT-EGFP.

In the meanwhile, the whole cell proteins in 1-mL aliquot of the bacterial culture with or without IPTG induction were obtained, followed by evenly admixing with same volume of 2× sample loading buffer (0.12 M Tris-HCl (pH 6.8), 4.4% (w/v) SDS, 10% (v/v) glycerol, 10% (v/v) 2-mercaptoethanol, and 2% bromophenol blue in deionized water). The resultant mixture was heated in a boiling water bath for 5 min and then used as a protein sample in protein analysis by sodium dodecyl sulfate-polyacrylamide gel electrophoresis (SDS-PAGE) described below.

The remainder of the bacterial culture with or without IPTG induction was subjected to an intein self-cleavage process as described below.
B. Induction of DnaB Intein Self-Cleavage A 40-mL aliquot of the bacterial culture with or without IPTG induction was centrifuged at 8000 rpm for 10 min. The pellet thus collected was washed twice with a washing buffer (20 mM Tris-HCl, 1 mM EDTA and 1 M NaCl, pH 8.5), re-suspended in 10 mL of a reaction buffer (20 mM Tris-HCl, 1 mM EDTA and 1 M NaCl, pH 7.5), and incubated at 37° C. with shaking (50 rpm), so as to induce DnaB intein self-cleavage. After a designated time period (1-5 days), the resultant mixture was centrifuged at 12,000 rpm for 1 min. Protein samples as respectively prepared from the pellet and the supernatant thus collected were subjected to SDS-PAGE analysis and EGFP fluorescent analysis.

In another experiment, a 40-mL aliquot of the bacterial culture with or without IPTG induction was centrifuged at 8000 rpm for 10 min. The pellet thus collected was washed twice with a washing buffer (20 mM Tris-HCl, pH 7, with 1 mM EDTA and 1% NaCl), re-suspended in a reaction buffer (20 mM Tris-HCl, pH 10, with 1 mM EDTA and 1% NaCl), and incubated at 37° C. with shaking (50 rpm). After a designated time period (1-5 days), the resultant mixture was centrifuged at 12,000 rpm for 1 min. The pellet and the supernatant thus collected were subjected to a protein extraction treatment, respectively, followed by SDS-PAGE analysis and EGFP fluorescent analysis.

C. Analytical Methods
SDS-PAGE Analysis

This experiment was performed substantially according to the procedures set forth in U. K. Laemmli (1970), *Nature*, 227:680-685 using a Mini-Protein Tetra electrophoresis system (Bio-Rad).

Briefly, to a two-layered polyacrylamide gel consisting of a 12% SDS-PAGE separating gel and a 5% SDS-PAGE stacking gel on top of said separating gel, a 10 µL aliquot of each of the protein samples was loaded into a sample well formed at the top region of the stacking gel and electrophoresis was performed using a 1× running buffer (3.03 g Tris hydroxymethyl aminomethane, 14.4 g glycine and 1 g SDS, prepared in 1 L ddH$_2$O) at a voltage of 70 V for 0.3 hr, followed by running at a voltage of 140 V for 1.3 hrs. After electrophoresis, the gel was analyzed by Coomassie brilliant blue R-250 stain.

EGFP Fluorescent Analysis

The presence of EGFP in the solution was detected by a fluorescence spectrometer (Hitachi F-2500) with excitation at 488 nm and emission at 510 nm. A His-tag binding resin (Fractogel, Novagen Co., USA) was used to purify the EGFP from the supernatant containing EGFP protein. The purification steps followed the procedure listed in the User Protocol TB462 (Novagen) with the nickel metal ion as the ligand (C. Mateo et al., *Journal of Chromatography A*, Volume 915, Issues 1-2, 27 Apr. 2001, pp. 97-106). The obtained EGFP was used to build a calibration curve. The concentration of EGFP was calculated according to the calibration curve. The EGFP recovery is defined as the EGFP amount obtained in supernatant divided by the total EGFP amount in host cell and expressed as percentage. The purity of the EGFP was also rechecked with the computer software (Totallab, v2.01) via the image scanning on the harvested EGFP protein to that of the purified EGFP in SDS-PAGE.

All experiments were performed in triplicate and analyzed with the SAS program (version 6.12) to obtain the statistical results. The results are expressed as mean±SD (n=3).

Figure 3:
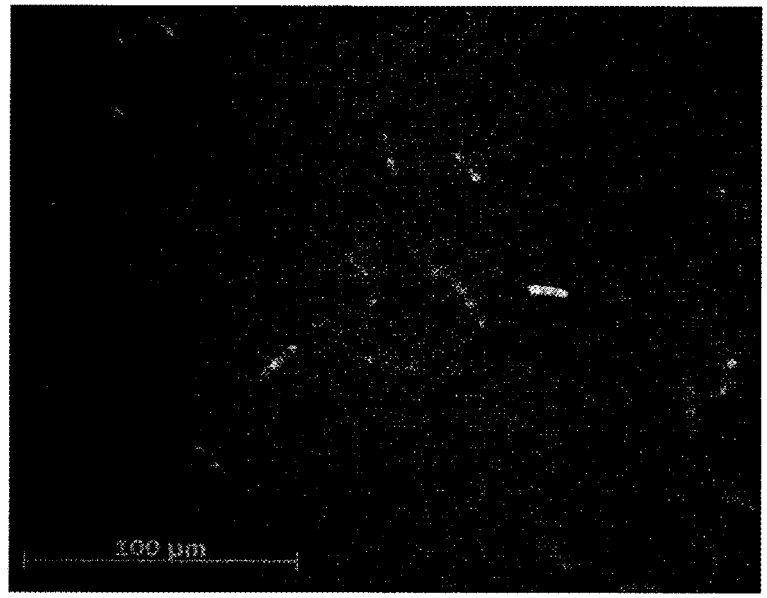
FIG. 3 is a photomicrograph showing the morphology of IPTG-induced E. coli DH1(DE3)/pINPNC-INT-EGFP cells, as observed using a fluorescent microscope at an excitation wavelength of 488 nm and an emission wavelength of 510 nm, in which scale bar=100 μm.

Results:

1. Expression of the Fusion Protein INPNC-INT-EGFP and Release of EGFP from the Fusion Protein INPNC-INT-EGFP FIG. 3 is a photomicrograph showing the morphology of IPTG-induced *E. coli* DH1(DE3)/pINPNC-INT-EGFP cells, as observed using a fluorescent microscope at an excitation wavelength of 488 nm and an emission wavelength of 510 nm. It can be seen from FIG. 3 that the bacterial cells exhibited green fluorescence, indicating that IPTG induced the bacterial cells to express the fusion protein INPNC-INT-EGFP, which in turn was anchored on the bacterial cells' outer membranes by virtue of the function of the INPNC segment thereof. The observed green fluorescence verified that the EGFP segment in the expressed fusion protein was active to emit green fluorescence.

Figure 4:
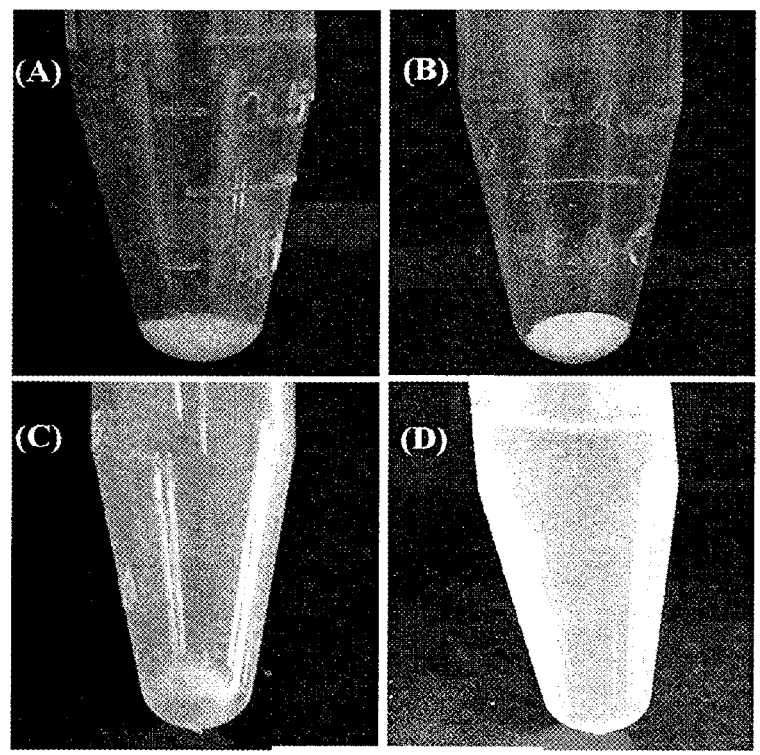
FIG. 4 shows the effects of IPTG induction and intein self-cleavage on E. coli DH1(DE3)/pINPNC-INT-EGFP cells, in which panel A, the pellet of bacterial cells without IPTG induction; panel B, the pellet of the bacterial cells with IPTG induction; panel C, the pellet of the IPTG-induced bacterial cells with intein self-cleavage treatment; and panel D, the supernatant of the IPTG-induced bacterial cells with intein self-cleavage treatment.

Referring to FIG. 4, no green fluorescence was visually observed for the pellet of bacterial cells without IPTG induction (panel A). In contrast, the pellet of the bacterial cells with IPTG induction exhibited green fluorescence (panel B). When the bacterial cells with IPTG induction was subjected to an intein self-cleavage process using a mild pH change from 8.5 to 7.5, followed by centrifugation, no green fluorescence was observed for the resultant pellet (panel C), whereas the corresponding supernatant exhibited a light green fluorescence (panel D).

Figure 5:
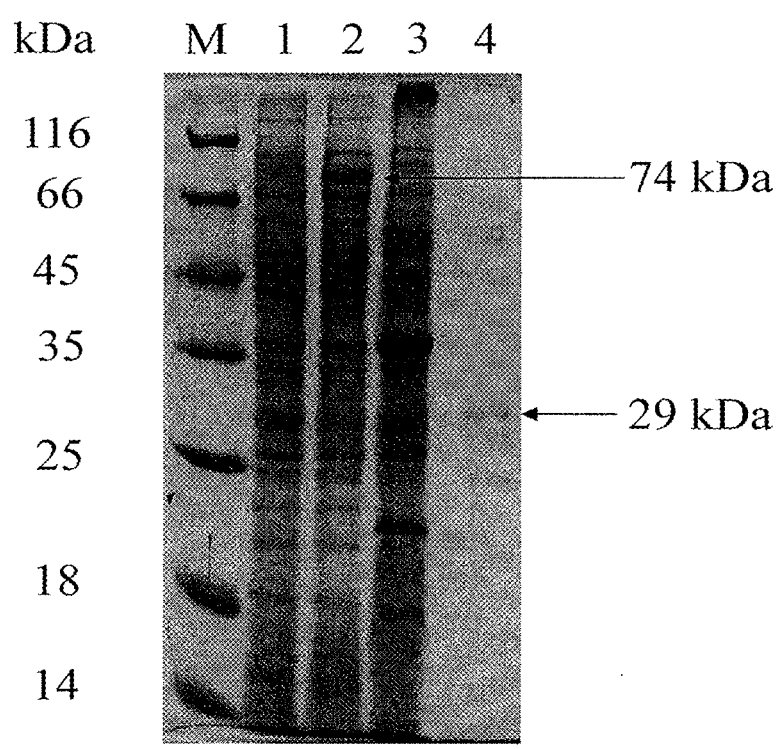
FIG. 5 is a protein electrophoresis graph showing the electrophoretic results of the protein sample of E. coli DH1(DE3)/pINPNC-INT-EGFP cells without IPTG induction (lane 1), the protein sample of the IPTG-induced bacterial cells without intein self-cleavage treatment (lane 2), the protein sample of the IPTG-induced bacterial cells that had been subjected to an intein self-cleavage process using a pH change from 8.5 to 7.5 (lane 3), and the protein sample of the supernatant of said IPTG-induced bacterial cells that had been subjected to the intein self-cleavage treatment, in which M represents protein ladder marker (116, 66, 45, 35, 25, 18 and 14 kDa)

The pellet of the bacterial cells without IPTG induction, the pellets of the IPTG-induced bacterial cells with and without an intein self-cleavage treatment using a mild pH change from 8.5 to 7.5 and the supernatant collected after intein self-cleavage treatment were subjected to a protein analysis by SDS-PAGE, followed by Coomassie brilliant blue R-250 stain. Referring to FIG. 5, as compared to the bacterial cells without IPTG induction (lane 1), the protein sample of the IPTG-induced bacterial cells without intein self-cleavage treatment (lane 2) had an obvious additional protein band located at around 74 kDa. According to the molecular weights of INPNC, DnaB intein and EGFP (27 kDa, 18 kDa and 29 kDa, respectively), the recombinant fusion protein INPNC-INT-EGFP was estimated to have a molecular weight of around 74 kDa. Inasmuch as the bacterial culture was observed to exhibit green fluorescence under fluorescent microscopy after IPTG induction while no green fluorescence was found in the bacterial culture without IPTG induction, the protein band located at 74-kDa was accordingly the recombinant fusion protein INPNC-INT-EGFP. The 74-kDa protein band was not found in the protein sample of the IPTG-induced bacterial cells with intein self-cleavage treatment (lane 3), and the protein sample of the supernatant was found to have an obvious protein band located at 29-kDa (lane 4), indicating that EGFP was released from the fusion protein INPNC-INT-EGFP without disruption of the bacterial cells.

Figure 6:
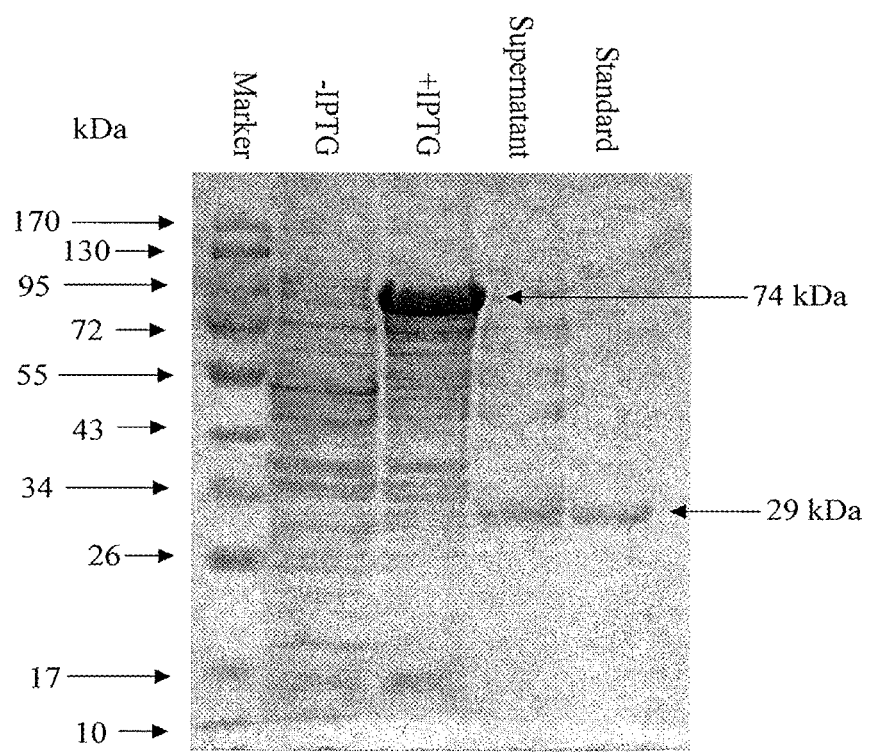
FIG. 6 is a protein electrophoresis graph showing the electrophoretic results of the protein sample of E. coli DH1(DE3)/pINPNC-INT-EGFP cells without IPTG induction (the lane marked with "−IPTG"), the protein sample of the IPTG-induced bacterial cells without intein self-cleavage treatment (the lane marked with "+IPTG"), the protein sample of the IPTG-induced bacterial cells that had been subjected to an intein self-cleavage process using a pH change from 7 to 10, and the protein sample of the supernatant of said IPTG-induced bacterial cells that had been subjected to the intein self-cleavage treatment (the lane marked with "Supernatant"), and resin-purified EGFP (the gel lane marked with "Standard"), in which Marker represents protein ladder marker (170, 130, 95, 72, 55, 43, 34, 26, 17 and 10 kDa)

A separate experiment similar to that of FIG. 5 was performed in which the IPTG-induced *E. coli* DH1(DE3)/pINPNC-INT-EGFP cells were subjected to an intein self-cleavage process using a pH change from 7 to 10. It can be seen from FIG. 6 that when the IPTG-induced bacterial cells were subjected to an intein self-cleavage process under a different pH range (from pH 7 to pH 10), EGFP could still be released from the expressed fusion protein INPNC-INT-EGFP.

In this experiment, the efficiency of EGFP production was also analyzed. The total EGFP amount expressed in bacterial cells was analyzed after 24-hr ITPG induction. In addition, the EGFP amount harvested in the supernatant after the intein self-cleavage was also recorded (see FIG. 7, panel A). The EGFP recovery (defined as the EGFP amount obtained in supernatant divided by the total EGFP amount in host cell and expressed as percentage) was calculated (see FIG. 7, panel B).

Figure 7:
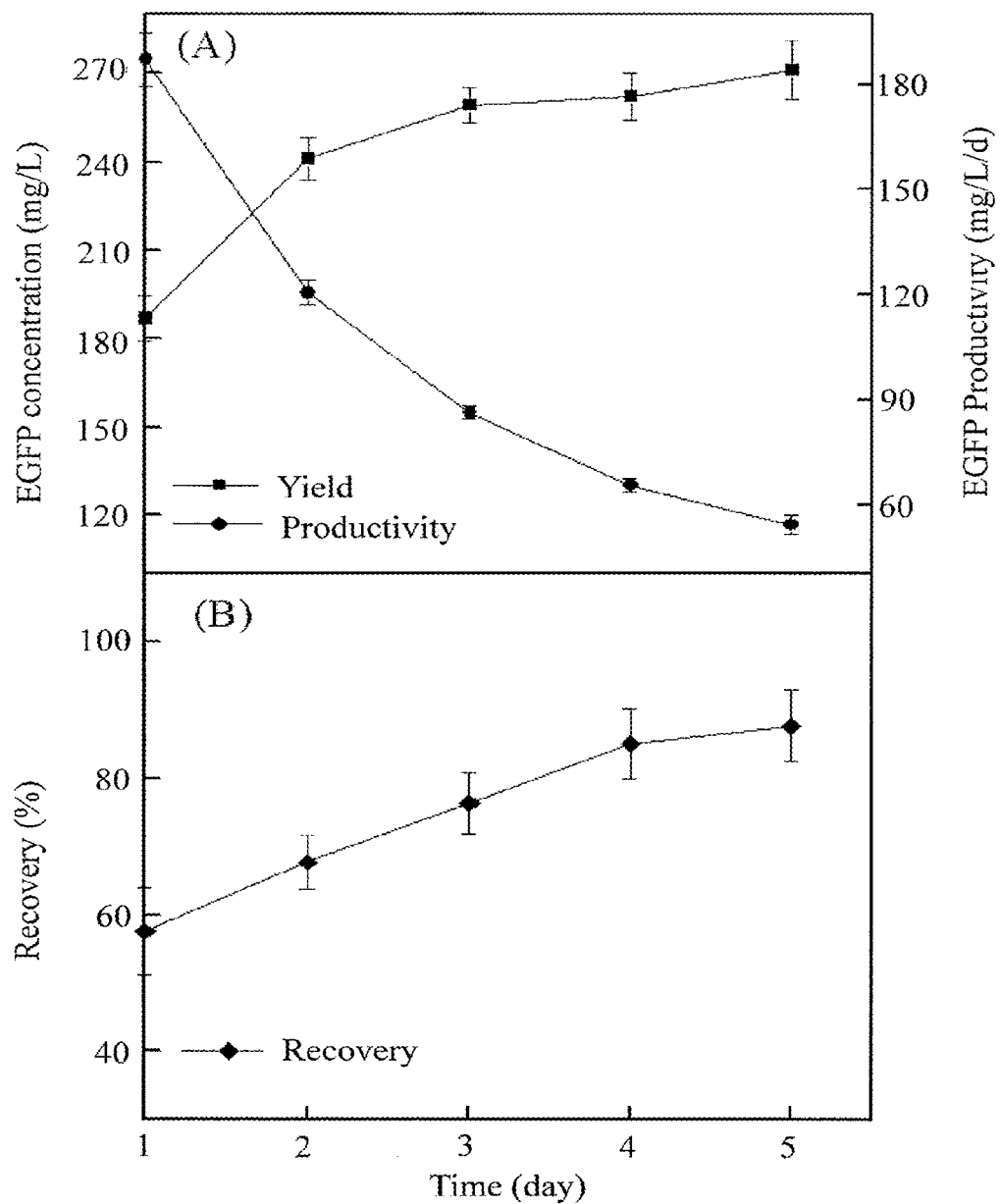
FIG. 7 shows the time courses of EGFP production, where (■) represents EGFP concentration, (●) is the EGFP productivity, and (◆) is the EGFP recovery.

The EGFP recovery of 58±6(%) (concentration of 187 mg/L) was obtained for a 24-hr cleaving incubation. For a 5-day incubation, the EGFP recovery could reach 88±5(%) with the concentration of 273 mg/L. It is noted that the highest productivity of 187 mg/L/d appeared at Day 1 (FIG. 7, panel A). A longer incubation time would result in a rapid drop in the productivity. Therefore, it is concluded that a 1-day cleavage process is better for the EGFP productivity.

In the intein data book (IMPACT™-CN Instruction manual, New England Biolabs, Beverly, Mass.), the production of GFP via the expression of chitin binding domain (CBD)-intein-GFP in *E. coli*, followed by a series of chromatographic steps, a production concentration of 1.9 mg/L was obtained. Meanwhile, Bateman cultivated recombinant *Acanthamoeba* sp. to produce EGFP and the production concentration was approximately 50 mg/L (E. Bateman et al. (2010), *Protein Expr. Purif.*, 70:95-100). Dieryck et al. used His-tag and two steps purification (immobilized metal affinity expanded bed adsorption and size exclusion chromatography) to obtain 230 mg/L EGFP (W. Dieryck et al. (2003), *J. Chromatogr. B*, 786:153-159). In the study of this invention, by constructing and expressing the fusion gene INP-INT-EGFP in *E. coli*, followed by a two-step centrifugation without any cell disruption or affinity chromatographic process, an EGFP concentration of 273 mg/L can be easily obtained.

To further check the purity of EGFP (defined as the EGFP amount divided by the total protein amount) obtained in this approach, the harvested EGFP in the supernatant (at Day 5) was analyzed by applying the computer software (Totallab, v2.01) on Lane 4 of the gel shown in FIG. 5 and a purity value of 50.5% was obtained. In addition, the same software analysis was applied to the protein sample of the IPTG-induced cells on Lane 3 of the same gel, and it was observed that only an EGFP purity of 8.5% (calculation based on the color intensity of the protein band at 74 kDa) was obtained in the original crude extract, indicating that a 6-fold protein purification was achieved just by a simple centrifugation step without any extensive purification process.

Although the protein production process exemplified above is quite preliminary, it provides a simple and rapid way to yield protein with proper purity. It is expected that the protein thus obtained may be directly applied in some industrial applications. Therefore, it is still beneficial to obtain protein by this approach without a series of purification steps or via a laborious affinity purification procedure. However, in some other cases such as in medical use, further purification steps are still needed if the protein with a higher purity is required. Further developments in this regard are worthwhile.

Example 3

The Influence of pH and Temperature on the DnaB Intein Self-Cleavage

A. The Influence of pH on the DnaB Intein Self-Cleavage

The cells of *E. coli* transformant DH1(DE3)/pINPNC-INT-EGFP as obtained in Example 1 were inoculated into 40 mL of the LB broth containing 50 µg/mL kanamycin and cultivated at 37° C. with shaking (150 rpm). After reaching a cell density of about 1 ($OD_{600}$), the bacterial culture was added with IPTG to a final concentration of 1 mM, and then cultivated at 18° C. (to prevent protein aggregation) with shaking (150 rpm) for further 24 hrs, so as to induce the bacterial cells to express the fusion protein INPNC-INT- EGFP. The resultant bacterial culture was then centrifuged at 8000 rpm for 10 min. The pellet thus collected was washed twice with the washing buffer (pH 8.5), re-suspended in 10 mL of the reaction buffer having a designated pH (pH 6, 7, 8, 9 or 10), and incubated at 37° C. with shaking (50 rpm), so as to induce DnaB intein self-cleavage. At a designated incubation time (from 0 day to 8 days), a 1 mL aliquot of the resultant mixture was centrifuged at 12,000 rpm for 3 min, and the supernatant was harvested and subjected to fluorescence emission assay using a fluorescence spectrophotometer (F-2500, Hitachi) operated under the following conditions: excitation wavelength, 488 nm; emission wavelength, 500-520 nm; Ex slit and Em slit, 2.5 nm; and voltage, 400 V. The results are shown in FIG. 8.

Figure 8:
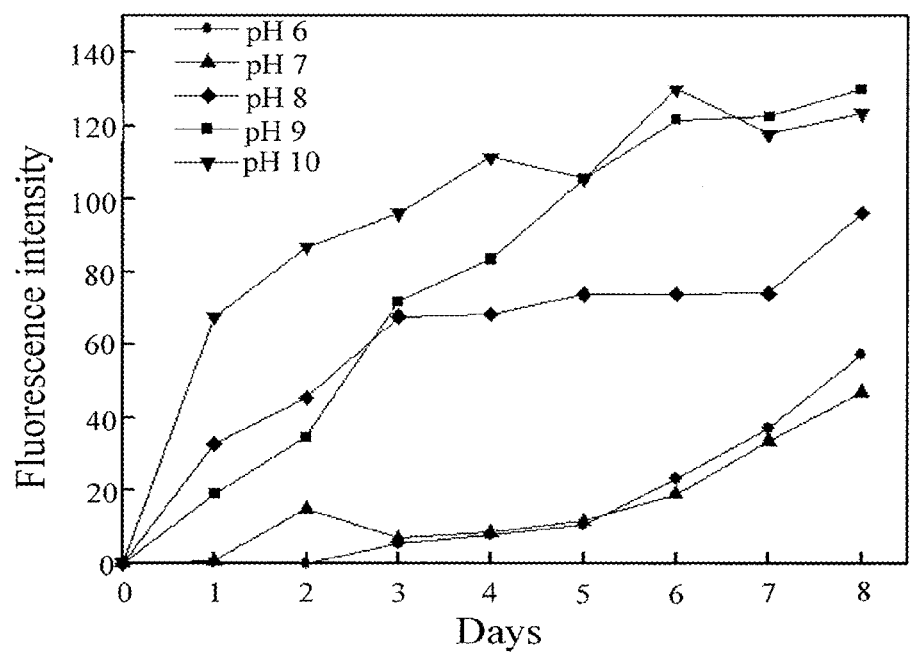
FIG. 8 shows the change of fluorescence intensity with time in IPTG-induced E. coli DH1(DE3)/pINPNC-INT-EGFP cells that had been transferred to an incubation condition having a pH of 6, 7, 8, 9 or 10.

Results:

The experimental results shown in FIG. 8 reveal that, when the IPTG-induced *E. coli* DH1(DE3)/pINPNC-INT-EGFP cells were transferred to an incubation condition having a pH of 6, 7, 8, 9 or 10, the fluorescence intensity increased with time. Particularly, when the IPTG-induced bacterial cells were transferred to an incubation condition having a pH of 8, 9 or 10 and incubated one day, the fluorescence intensity started to significantly increase with time. When the IPTG-induced bacterial cells were transferred to an incubation condition having a pH of 6 or 7, a significant increase of the fluorescence intensity was observed at Day 6. The obtained results reveal that when IPTG-induced *E. coli* DH1(DE3)/pINPNC-INT-EGFP cells were transferred to an incubation condition having a pH ranging from 8 to 10, the DnaB intein self-cleavage was enhanced to release more EGFP.

The applicants presume that: the fusion protein INPNC-INT-EGFP expressed by IPTG-induced *E. coli* DH1(DE3)/pINPNC-INT-EGFP cells was constructed to consist of three segments, namely a 27-kDa truncated INP, an 18-kDa DnaB intein and a 29-kDa EGFP. The truncated INP was composed of the N-terminal and C-terminal domains of INP and, hence, had a length shorter than that of the intact INP. As such, when the fusion protein INPNC-INT-EGFP was expressed and anchored on the outer membranes of the IPTG-induced *E. coli* DH1(DE3)/pINPNC-INT-EGFP cells, the DnaB intein segment would be rather closer to the bacterial cells' outer membranes, where the glycosides and/or membrane proteins existing thereon would form steric hindrance to interfere with the DnaB intein self-cleavage. However, since the lipid bilayers of the bacterial cells' outer membranes are liable to alkali attack, when the IPTG-induced *E. coli* DH1(DE3)/pINPNC-INT-EGFP cells were transferred to an incubation condition having a pH ranging from 8 to 10, the steric hindrance caused by the glycosides and/or membrane proteins existing on the bacterial cells' outer membranes might be eliminated, thus enhancing the DnaB intein self-cleavage.

B. The Influence of Temperature on the DnaB Intein Self-Cleavage

The cells of *E. coli* transformant DH1(DE3)/pINPNC-INT-EGFP as obtained in Example 1 were inoculated into 40 mL of the LB broth containing 50 μg/mL kanamycin and cultivated at 37° C. with shaking (150 rpm). After reaching a cell density of about 1 ($OD_{600}$), the bacterial culture was added with IPTG to a final concentration of 1 mM, and then cultivated at 18° C. (to prevent protein aggregation) with shaking (150 rpm) for further 24 hrs, so as to induce the bacterial cells to express the fusion protein INPNC-INT-EGFP. The resultant bacterial culture was then centrifuged at 8000 rpm for 10 min. The pellet thus collected was washed twice with the washing buffer (pH 8.5, 25° C.), re-suspended in 10 mL of the reaction buffer (pH 9.0), and incubated at a designated temperature (15° C., 25° C., 30° C. and 37° C.) with shaking (50 rpm), so as to induce DnaB intein self-cleavage. At a designated incubation time (from 0 day to 8 days), a 1 mL aliquot of the resultant mixture was centrifuged at 12,000 rpm for 3 min, and the supernatant was harvested and subjected to fluorescence emission assay as described above. The results are shown in FIG. 9.

Figure 9:
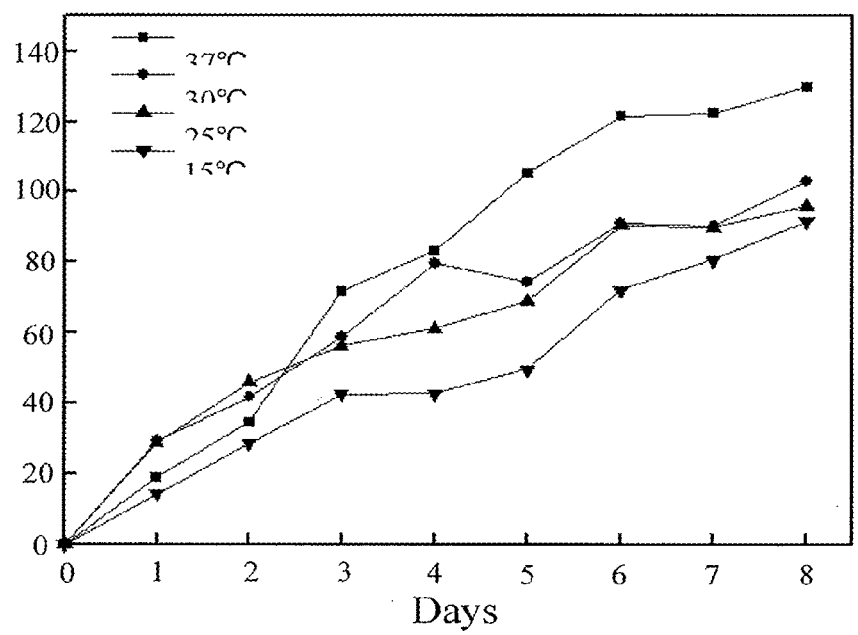
FIG. 9 shows the change of fluorescence intensity with time in IPTG-induced E. coli DH1(DE3)/pINPNC-INT-EGFP cells that had been transferred to an incubation condition having a temperature of 15☐, 25☐, 30☐ or 37° C.

Results:

The experimental results shown in FIG. 9 reveal that, when the IPTG-induced *E. coli* DH1(DE3)/pINPNC-INT-EGFP cells were transferred to an incubation condition having a temperature of 15° C., 25° C., 30° C. or 37° C., the fluorescence intensity increased with time. At the first four days, a similar increase of fluorescence intensity was observed for all of the incubation temperatures. However, starting from Day 5, the IPTG-induced *E. coli* DH1(DE3)/pINPNC-INT-EGFP cells incubated at 37° C. was found to have a significant increase of fluorescence intensity. The obtained results reveal that an incubation temperature of 37° C. could enhance the DnaB intein self-cleavage, thereby increasing the release of EGFP.

Example 4

Construction of Recombinant Vector pINP-INT-Dht

In this example, the applicant tested the applicability of the INP-INT expression cassette of this invention in the production of D-hydantoinase, which is known to have great utility in the industry, e.g., in the production of D-amino acids, such as D-p-hydroxyphenylglycine (D-p-HPG), a precursor of Amoxicillin and Cefadroxil.

A. Production of Plasmid pT-INT-Dht

Based on the nucleotide sequence of the Ssp dnaB gene (referred to as INT gene in this experiment) located in the plasmid pTWIN1 and the nucleotide sequence of the dht gene located in the plasmid pQE-bcdht, the four primers as shown in the following Table 5 were designed:

TABLE 5

Primers used in the production of the INT-Dht fusion gene via PCR reaction

| Primer | Nucleotide sequence (5'→3') |
|---|---|
| pTWIN1 INT F | EcoRI<br>ccg<u>gaattc</u>ctgcgcgagtccggag (SEQ ID NO: 8) |
| pTWIN1 INT R | EagI<br>ccg<u>cggccg</u>ttgtgtacaatgatgtc (SEQ ID NO: 9) |
| Dht F | EagI<br>ccg<u>cggccg</u>ggcgatgaaaaaatggattcgc (SEQ ID NO: 10) |

TABLE 5-continued

Primers used in the production of the INT-Dht fusion gene via PCR reaction

| Primer | Nucleotide sequence (5'→3') |
|---|---|
| Dht R | XhoI<br>ccg<u>ctcgag</u>tggtctggcaaacgtc (SEQ ID NO: 11) |

Note:
The underlined nucleotides represent the recognition site of a restriction enzyme as indicated above.

With the plasmid pTWIN1 as a template, a first PCR product of about 0.5 kbp that contained an INT gene encoding the DnaB intein was amplified by PCR reactions using primers pTWIN1 INT F and pTWIN1 INT R. In the meantime, with the plasmid pQE-bcdht as a template, a second PCR product of about 1.4 kbp that contained a dht gene encoding D-hydantoinase was amplified by PCR reactions using primers Dht F and Dht R. The recovered first and second PCR products were then cloned into the yT&A vector using the TA Cloning Kit (Yeastern Biotech. Co., Ltd., Taiwan), respectively, followed by transforming into competent *E. coli* DH5α cells. The plasmid DNAs extracted from the resultant transformants were analyzed by PCR reactions using the aforesaid four primers to verify the existence of the target gene (i.e., the INT gene or the dht gene) therein. According to a sequencing analysis conducted by Tri-I Biotech, Inc., recombinant plasmids pT-INT and pT-Dht that were verified to contain the INT gene segment and the dht gene, respectively, were obtained.

Thereafter, a cleavage product, which was obtained by cleaving the recombinant plasmid pT-INT with restriction enzymes EcoRI and EagI and which contained the INT gene, was ligated with the EagI-treated plasmid pT-Dht, and the resultant ligated product was transformed into competent *E. coli* DH5α cells. After plasmid screening by PCR reactions using the primers pTWIN1 INT F and Dht R as well as sequencing analysis, a recombinant plasmid pT-INT-Dht (4,597 bps) that was verified to contain an INT-dht fusion gene was obtained.

B. Construction of Recombinant Plasmid pINP-INT-Dht

Figure 10:
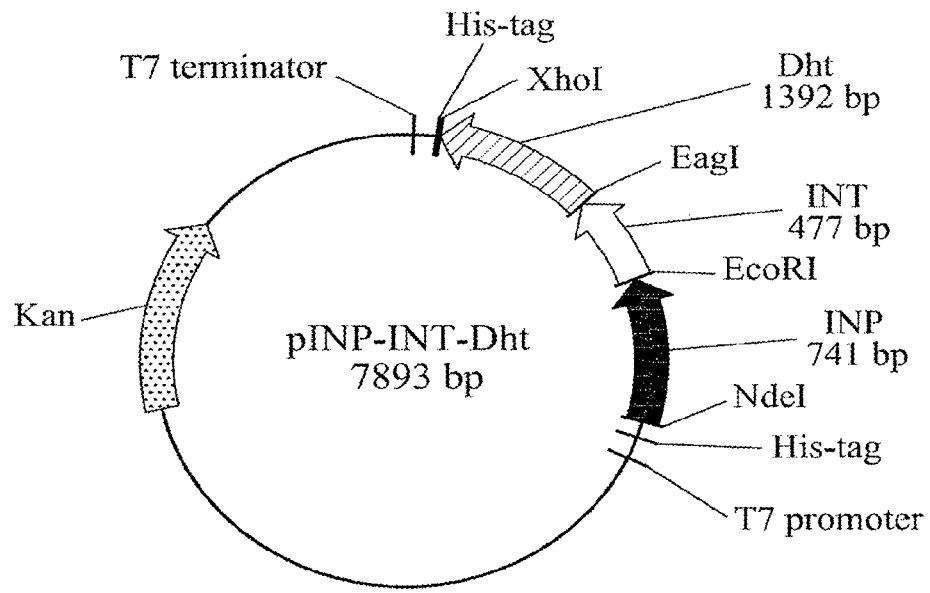
FIG. 10 shows the construct of recombinant plasmid pINP-INT-Dht, which carries a fusion gene consisting of an INP gene, an INT gene and a dht gene along the transcription direction; in which Kan represents kanamycin resistance gene; and NdeI, EcoRI, EagI and XhoI represent the recognition sites of the corresponding restriction enzymes, respectively.

The recombinant plasmid pT-INT-EGFP as obtained in the preceding section A was cleaved with restriction enzymes EcoRI and XhoI so that a first cleavage product (1,869 bps) containing the INT-dht fusion gene was obtained. In the meantime, plasmid pInaXNC-aglA2 was cleaved with restriction enzymes EcoRI and XhoI so that a second cleavage product containing the inaNC gene (referred to as "INP gene" in this example) was obtained. The first and second cleavage products were subsequently ligated, and the resultant ligated product was transformed into competent *E. coli* ER2566 cells. After plasmid screening by PCR reactions using the primers pTWIN1 INT F and Dht R as well as sequencing analysis, a recombinant plasmid pINP-INT-Dht that was verified to contain an INP-INT-dht fusion gene was obtained. The recombinant plasmid pINP-INT-Dht (7,893 bps) was determined to have a plasmid construct as shown in FIG. 10. The *E. coli* transformant harboring the recombinant plasmid pINP-INT-Dht was named "*E. coli* ER2566/pINP-INT-Dht."

C. Production of D-hydantoinase from Fusion Protein INP-INT-Dht Expressed by *E. coli* ER2566/pINP-INT-Dht The cells of *E. coli* ER2566/pINP-INT-Dht as obtained in the preceding section B were cultivated in 50 mL of the LB broth containing 50 μg/mL kanamycin at 37° C. with shaking (150 rpm). After overnight cultivation, 10 mL of the bacterial culture was inoculated into 90 mL of the LB broth containing 50 μg/mL kanamycin in a ratio of 1:10 and cultivated at 37° C. with shaking (200 rpm). After reaching a cell density of about 0.6 ($OD_{600}$), the bacterial culture was added with IPTG to a designated final concentration (0.05, 0.5 and 1 mM), and then cultivated at 15° C. with shaking (200 rpm) for further 24 hrs, so as to induce the bacterial cells to express the fusion protein INPNC-INT-EGFP. The total protein of the IPTG-induced bacterial cells was analyzed by SDS-PAGE, and that of bacterial culture without IPTG induction was used as a control.

The IPTG-induced bacterial cells were centrifuged at 4° C. at 6,000 rpm for 5 min, and the pellet thus collected was re-suspended in 10 mL of reaction buffer (50 mM Tris-HCl, pH 6.0) and incubated at 25° C. with shaking (100 rpm), so as to induce intein self-cleavage. After 24 hr incubation, the resultant mixture was centrifuged at 12,000 rpm for 1 min, and the supernatant thus collected was subjected to D-hydantoinase activity assay described below.

C. Detection of D-hydantoinase (Dht) Activity

To a glass tube was added a 500 μL aliquot of the supernatant as obtained in the preceding section B, followed by admixing with 500 μL of 10 mM 5-(4-hydroxyphenyl) hydantoin in 0.1 M Tris-HCl buffer (pH 8.0). The glass tube was incubated in a 50° C. water bath for 15 min, followed by heating in boiled water for 10 min, so as to terminate reaction. The resultant mixture was centrifuged at 12,000 rpm for 5 min, and a 50 μL aliquot of the supernatant thus obtained was mixed with 950 μL dd$H_2O$ and then filtered with a 0.2 μm filter membrane. The filtrate thus obtained was analyzed by HPLC (RI-930, JUSCO, Japan) using a reversed phase BDS HYPERSIL column of 250 mm×4.6 mm, running with a mobile phase consisting of 5% acetonitrile and 0.01% $H_3PO_4$ (aq) at a flow rate of 1 mL/min, and detected by a UV detector set at 230 nm.

Results:

In this example, a recombinant plasmid pINP-INT-Dht that contained a plasmid construct as shown in FIG. 10 was obtained. According to the molecular weights of INP, INT and Dht (27 kDa, 18 kDa and 29 kDa, respectively), the recombinant plasmid pINP-INT-Dht was expected to express a recombinant protein of around 97 kDa. To verify the ability of the recombinant plasmid pINP-INT-Dht in expressing a protein of 97 kDa, the cells of *E. coli* ER2566/pINP-INT-Dht, a cloned transformant harboring the recombinant plasmid pINP-INT-Dht, were cultivated and subjected to IPTG induction.

Figure 11:
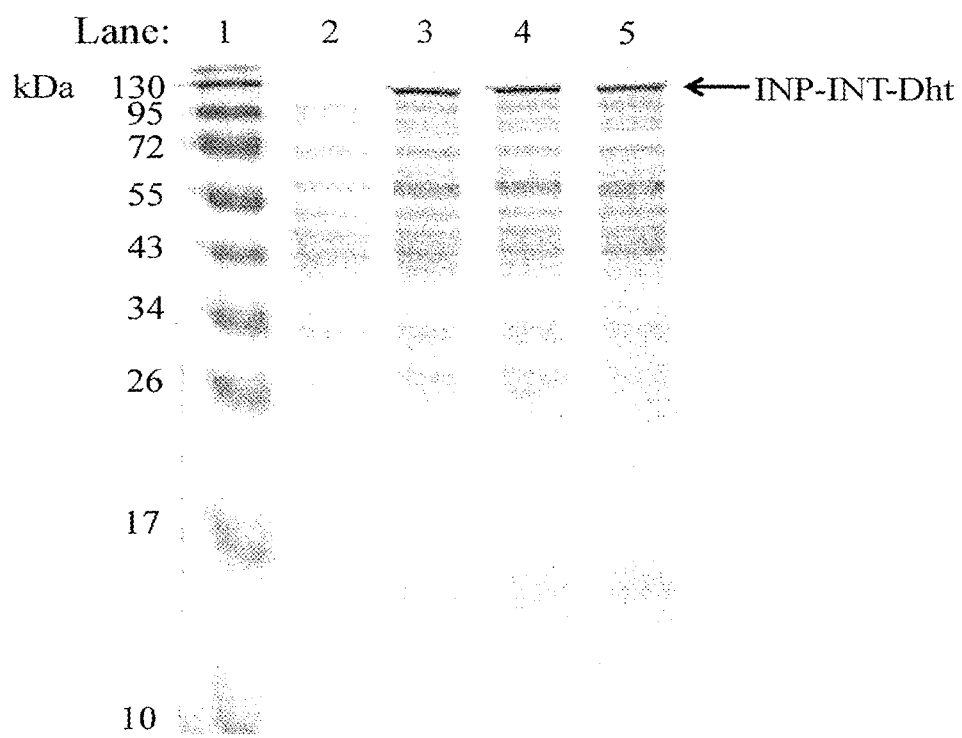
FIG. 11 is a protein electrophoresis graph showing the electrophoretic results of the protein samples of E. coli ER2566/pINP-INT-Dht cells with and without IPTG induction, in which lane 1: protein ladder marker (130, 95, 72, 55, 43, 34, 26, 17 and 10 kDa); lane 2: the protein sample of the bacterial cells without IPTG-induction; lanes 3-5: the protein samples of the bacterial cells with IPTG-induction at different concentrations (0.05, 0.5 and 1 mM)

Referring to FIG. 11, the protein sample of the IPTG-induced bacterial cells was found to have an additional protein located at around 97 kDa, as compared to that of the bacterial cells without IPTG induction. In addition, IPTG-induction at different concentrations (0.05, 0.5 and 1 mM) does not result in a significant difference in the expressed amounts of said 97 kDa protein. Thus, the bacterial cells induced with 0.05 mM IPTG were further subjected to D-hydantoinase activity assay.

Figure 12A:
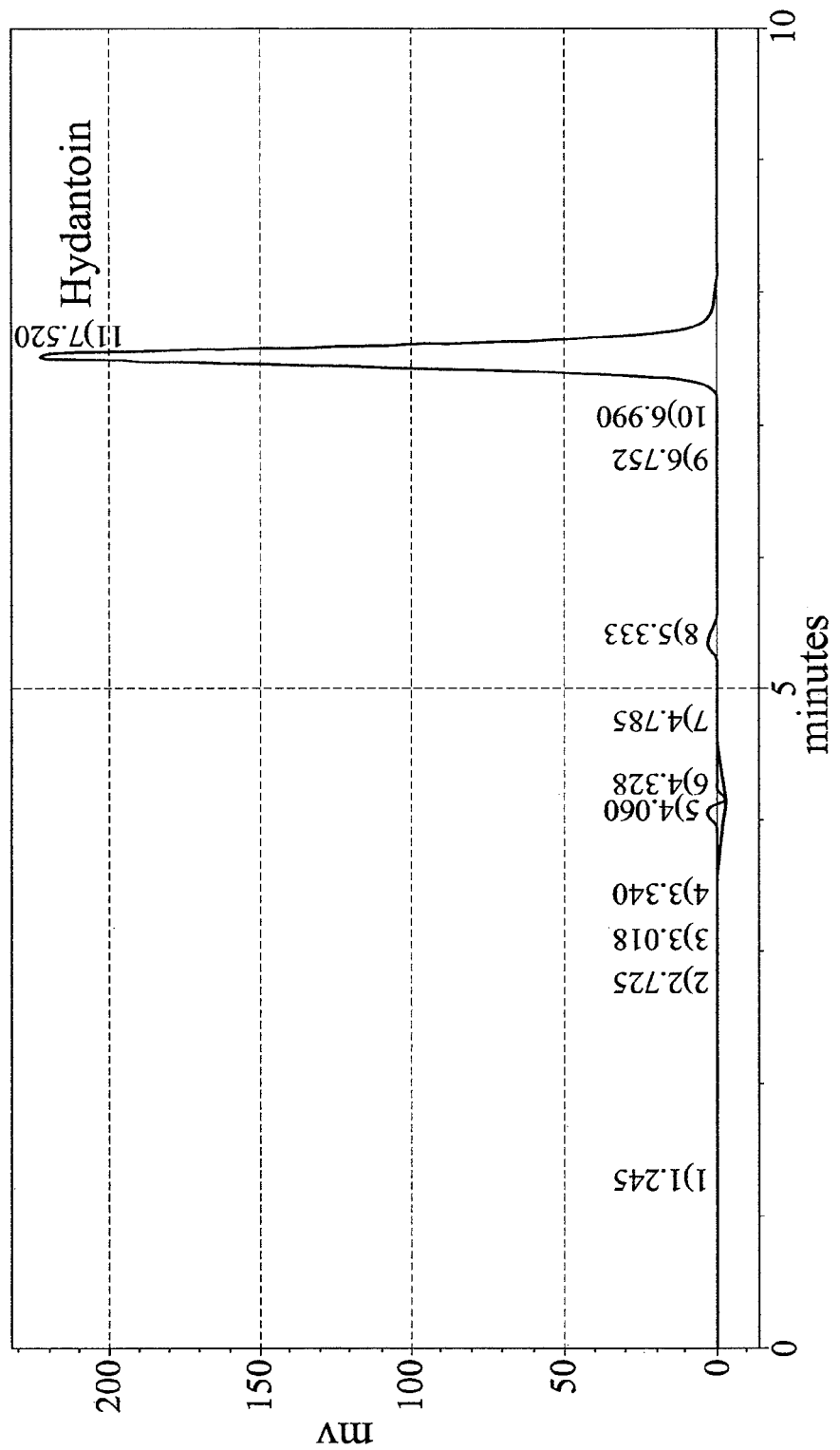
FIG. 12 shows the D-hydantoinase activity of a supernatant collected from IPTG-induced E. coli ER2566/pINP-INT-Dht cells after subjecting to a intein self-cleavage process (changing incubation temperature from 4° C. to 25° C.), as determined by HPLC analysis, in which upper panel, the HPLC chromatogram of a substrate solution containing 5-(4-hydroxyphenyl) hydantoin only; and lower panel, the HPLC chromatogram of the substrate solution after reaction with the supernatant (see Example 4, infra).
Figure 12B:
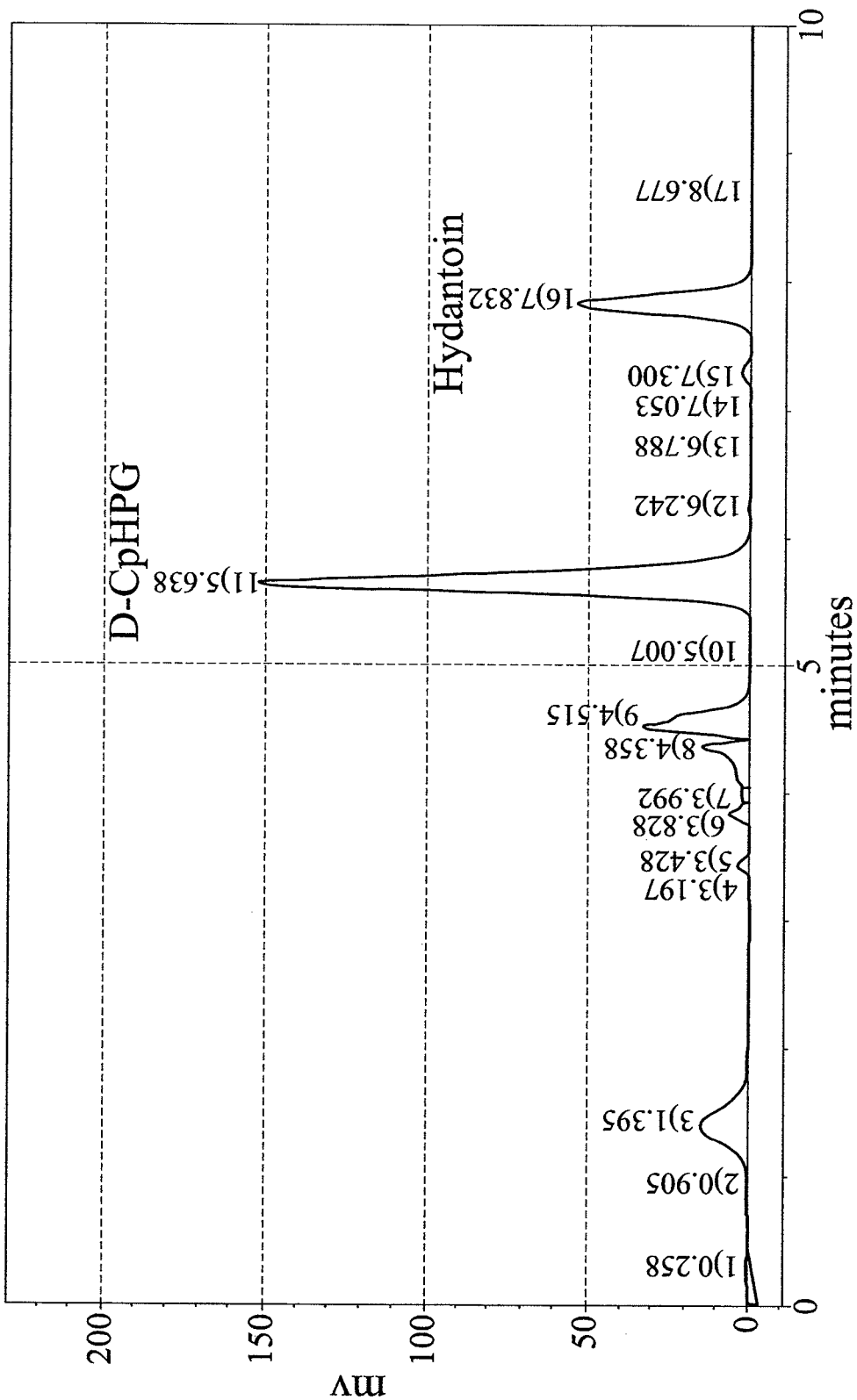

Referring to FIG. 12, a change of the incubation temperature from 4° C. to 25° C. resulted in an intein self-cleavage in the 97 kDa protein expressed by *E. coli* ER2566/pINP-INT-Dht cells induced with 0.05 mM IPTG, and the released D-hydantoinase as contained in the collected supernatant was active to convert 5-(4-hydroxyphenyl) hydantoin into an N-carbamoyl derivative, i.e., D-CpHGP shown in panel B.

The results of this example once again provide evidence that the INP-INT expression cassette according to this invention is useful in the production of target proteins.

All patents and literature references cited in the present specification as well as the references described therein, are hereby incorporated by reference in their entirety. In case of conflict, the present description, including definitions, will prevail.

While the invention has been described with reference to the above specific embodiments, it is apparent that numerous modifications and variations can be made without departing from the scope and spirit of this invention. It is therefore intended that this invention be limited only as indicated by the appended claims.

We claim:

1. A process for producing a target protein, comprising:
    providing a host cell having an outer membrane and harboring an expression cassette containing a recombinant polynucleotide therein, wherein the host cell is capable of expressing a fusion protein encoded by the recombinant polynucleotide and wherein the fusion protein comprises:
    (i) an anchoring protein that comprises a N-terminal amino acid sequence of an ice nucleation protein, so that the fusion protein, once expressed in the host cell, is directed by the anchoring protein to be anchored and exposed on the outer membrane of the host cell;
    (ii) the target protein; and
    (iii) a self-splicing protein that comprises a first end fused with the anchoring protein and a second end fused with the target protein, wherein the self-splicing protein comprises a N-terminal or C-terminal amino acid sequence of an intein protein at the second end thereof, such that upon an environmental stimulus, the self-splicing protein exerts a self-cleavage at the second end thereof to release the target protein from the fusion protein;
    obtaining a cell culture by culturing the host cell in a medium under a condition that enables the fusion protein to be expressed and anchored on the outer membrane of the host cell;
    subjecting the cell culture thus obtained to an environmental stimulus that induces the self-splicing protein to exert a self-cleavage at the second end thereof; and
    recovering the target protein by a separating treatment.

2. The process according to claim 1, wherein in the fusion protein encoded by the recombinant polynucleotide, the anchoring protein is a full-length or truncated ice nucleation protein.

3. The process according to claim 1, wherein in the fusion protein encoded by the recombinant polynucleotide, the self-splicing protein is an intein protein selected from the group consisting of Ssp DnaB intein, Ssp DnaE intein, Mxe GyrA intein, VMA intein, Mtu RecA intein, Psp Pol-I intein, PI-pful intein, PI-pfull intein, and Mth RIR1 intein.

4. The process according to claim 1, wherein the environmental stimulus that induces the self-splicing protein to exert a self-cleavage is selected from the group consisting of a pH change, a temperature change, a salt concentration, or a combination thereof.

5. The process according to claim 4, wherein the environmental stimulus that induces the self-splicing protein to exert a self-cleavage is a pH change, in which the cell culture is transferred from a first pH to a second pH, wherein the second pH is higher or lower than the first pH.

6. The process according to claim 5, wherein the environmental stimulus that induces the self-splicing protein to exert a self-cleavage is a pH change, in which the cell culture is transferred from pH 8.5 to pH 7.5.

7. The process according to claim 5, wherein the environmental stimulus that induces the self-splicing protein to exert a self-cleavage is a pH change, in which the cell culture is transferred from pH 7 to pH 10.

8. The process according to claim 4, wherein the environmental stimulus that induces the self-splicing protein to exert a self-cleavage is a temperature change, in which the cell culture is transferred from a first temperature ranging from 15° C. to 37° C. to a second temperature ranging from 18° C. to 37° C., wherein the second temperature is higher than the first temperature.

9. The process according to claim 4, wherein the environmental stimulus that induces the self-splicing protein to exert a self-cleavage is a temperature change, in which the cell culture is transferred from 18° C. to 37° C.

10. The process according to claim 1, wherein the expression cassette further comprises a promoter sequence selected from the group consisting of T7 promoter, T5 promoter, lac promoter, tac promoter, T7 A1 promoter, trp promoter, trc promoter, araBAD promoter, and $\lambda P_R P_L$ promoter.

11. The process according to claim 1, wherein the host cell is *E. coli*.

12. An expression cassette containing a recombinant polynucleotide encoding a fusion protein, wherein the fusion protein comprises:
(i) an anchoring protein that comprises a N-terminal amino acid sequence of an ice nucleation protein, so that the fusion protein, once expressed in a host cell transformed by the expression cassette, is directed by the anchoring protein to be anchored and exposed on the outer membrane of the host cell;
(ii) the target protein; and
(iii) a self-splicing protein that comprises a first end fused with the anchoring protein and a second end fused with the target protein, wherein the self-splicing protein comprises a N-terminal or C-terminal amino acid sequence of an intein protein at the second end thereof, such that upon an environmental stimulus, the self-splicing protein exerts a self-cleavage at the second end thereof to release the target protein from the fusion protein.

13. The expression cassette according to claim 12, wherein in the fusion protein encoded by the recombinant polynucleotide, the anchoring protein is a full-length or truncated ice nucleation protein.

14. The expression cassette according to claim 12, wherein in the fusion protein encoded by the recombinant polynucleotide, the self-splicing protein is an intein protein selected from the group consisting of Ssp DnaB intein, Ssp DnaE intein, Mxe GyrA intein, VMA intein, Mtu RecA intein, Psp Pol-I intein, PI-pful intein, PI-pfull intein, and Mth RIR1 intein.

15. The expression cassette according to claim 12, further comprising a promoter sequence operatively connected to the recombinant polynucleotide.

16. The expression cassette according to claim 15, wherein the promoter sequence is selected from the group consisting of T7 promoter, T5 promoter, lac promoter, tac promoter, T7 A1 promoter, tip promoter, trc promoter, araBAD promoter, and $\lambda P_R P_L$ promoter.

17. A recombinant host cell harboring an expression cassette containing a recombinant polynucleotide therein, wherein the host cell is capable of expressing a fusion protein encoded by the recombinant polynucleotide and wherein the fusion protein comprises:
(i) an anchoring protein that comprises a N-terminal amino acid sequence of an ice nucleation protein, so that the fusion protein, once expressed in the host cell, is directed by the anchoring protein to be anchored and exposed on the outer membrane of the host cell;
(ii) the target protein; and
(iii) a self-splicing protein that comprises a first end fused with the anchoring protein and a second end fused with the target protein, wherein the self-splicing protein comprises a N-terminal or C-terminal amino acid sequence of an intein protein at the second end thereof, such that upon an environmental stimulus, the self-splicing protein exerts a self-cleavage at the second end thereof to release the target protein from the fusion protein.

18. The recombinant host cell according to claim 17, wherein in the fusion protein encoded by the recombinant polynucleotide, the anchoring protein is a full-length or truncated ice nucleation protein.

19. The recombinant host cell according to claim 17, wherein in the fusion protein encoded by the recombinant polynucleotide, the self-splicing protein is an intein protein selected from the group consisting of Ssp DnaB intein, Ssp DnaE intein, Mxe GyrA intein, VMA intein, Mtu RecA intein, Psp Pol-I intein, PI-pful intein, PI-pfull intein, and Mth RIR1 intein.

20. The recombinant host cell according to claim 17, further comprising a promoter sequence operatively connected to the recombinant polynucleotide.

21. The recombinant host cell according to claim 20, wherein the promoter sequence is selected from the group consisting of T7 promoter, T5 promoter, lac promoter, tac promoter, T7 A1 promoter, tip promoter, trc promoter, araBAD promoter, and $\lambda P_R P_L$ promoter.

22. The recombinant host cell according to claim 17, which is an *E. coli* cell.

* * * * *